US008591923B2

(12) United States Patent
Mougin et al.

(10) Patent No.: US 8,591,923 B2
(45) Date of Patent: Nov. 26, 2013

(54) COSMETIC COMPOSITON COMPRISING A (THIO)URETHANE/(THIO)UREA COPOLYMER CAPABLE OF FORMING AT LEAST 3 HYDROGEN BONDS, AND A METHOD OF COSMETIC TREATMENT

(75) Inventors: Nathalie Mougin, Paris (FR); Xavier Schultze, Pontault-Combault (FR); Sandrine Chodorowski-Kimmes, Senlis (FR)

(73) Assignee: L'Oreal, Paris (FR)

( * ) Notice: Subject to any disclaimer, the term of this patent is extended or adjusted under 35 U.S.C. 154(b) by 1275 days.

(21) Appl. No.: 11/640,195

(22) Filed: Dec. 18, 2006

(65) Prior Publication Data
US 2007/0189991 A1 Aug. 16, 2007

Related U.S. Application Data

(60) Provisional application No. 60/754,184, filed on Dec. 28, 2005.

(30) Foreign Application Priority Data

Dec. 16, 2005 (FR) ..................................... 05 53913

(51) Int. Cl.
| A61Q 1/04 | (2006.01) |
| A61Q 1/10 | (2006.01) |
| A61Q 3/00 | (2006.01) |
| A61Q 5/06 | (2006.01) |
| A61Q 19/04 | (2006.01) |
| A61Q 19/10 | (2006.01) |

(52) U.S. Cl.
USPC ................ 424/401; 424/59; 424/61; 424/63; 424/64; 424/69; 424/70.1; 424/70.6; 424/70.7

(58) Field of Classification Search
None
See application file for complete search history.

(56) References Cited

U.S. PATENT DOCUMENTS

| 5,120,529 A | 6/1992 | Koch et al. |
| 6,395,265 B1 | 5/2002 | Mougin et al. |
| 2004/0052753 A1 | 3/2004 | Mougin |
| 2004/0161394 A1 | 8/2004 | Mougin et al. |
| 2004/0197293 A1 | 10/2004 | Mougin |
| 2005/0053571 A1 | 3/2005 | Hanada et al. |
| 2009/0111930 A1* | 4/2009 | van Gemert et al. .......... 524/498 |

FOREIGN PATENT DOCUMENTS

| EP | 0 391 322 B1 | 10/1990 |
| EP | 0 418 469 A1 | 3/1991 |
| EP | 1 031 589 A1 | 8/2000 |
| FR | 2 815 350 A1 | 4/2002 |
| FR | 2 821 621 A1 | 9/2002 |
| WO | WO 02/46260 A1 | 6/2002 |
| WO | WO 02/098377 A1 | 12/2002 |
| WO | WO 03/032929 A2 | 4/2003 |
| WO | WO 2004/052963 | * 6/2004 |
| WO | WO-2004/052963 A1 | 6/2004 |
| WO | WO-2005/042641 A1 | 5/2005 |

OTHER PUBLICATIONS

English language translation of Notice of Reasons for Rejection issued Mar. 13, 2012 in corresponding Japanese Application No. JP 2006-338330.
Kurt C. Frisch et al., "Polyurethanes," Comprehensive Polymer Science, The Synthesis, Characterization, Reactions & Applications of Polymers, vol. 5, Pergamon Press, pp. 413-426 (1989).
French Search Report for FR 0553913, dated Oct. 6, 2006.

* cited by examiner

*Primary Examiner* — Jyothsna Venkat
(74) *Attorney, Agent, or Firm* — Novak Druce Connolly Bove + Quigg LLP

(57) ABSTRACT

The present application relates to cosmetic compositions comprising, in a physiologically acceptable medium, a copolymer having a (thio)urethane/(thio)urea polymer skeleton, resulting from the reaction:
of a first monomer having at least two polymerizable groups, which may be identical or different, chosen from —N=C=O and —N=C=S,
of a monomer (b1) having at least two polymerizable groups with a labile hydrogen,
of a monomer (b2), different from monomer (b1), having at least two polymerizable groups with a labile hydrogen,
with at least one of these monomers comprising at least one junction group (A), capable of forming at least 3 hydrogen bonds.
The disclosure also relates to a method of cosmetic treatment of keratinous materials, comprising the application of a cosmetic composition as defined above on said materials.

25 Claims, No Drawings

COSMETIC COMPOSITON COMPRISING A (THIO)URETHANE/(THIO)UREA COPOLYMER CAPABLE OF FORMING AT LEAST 3 HYDROGEN BONDS, AND A METHOD OF COSMETIC TREATMENT

This application claims benefit of U.S. Provisional Application No. 60/754,184, filed Dec. 28, 2005, the contents of which are incorporated herein by reference. This application also claims benefit of priority under 35 U.S.C. §119 to French Patent Application No. FR 05 53913, filed Dec. 16, 2005, the contents of which are also incorporated herein by reference.

The present disclosure relates to cosmetic compositions for the care, treatment and/or make-up of keratinous materials, which can display increased persistence of at least one cosmetic and/or care effect provided by the composition after application.

In the field of cosmetics, it is desirable to obtain a deposit on the hair, the skin, the eyelashes and the nails, which is often film-forming and provides, for example, at least one of shaping of the hair; color (hair, make-up); shine; shine and color (lipstick, mascara, eye-liner and nail varnish); color and matte appearance (foundation, for example); and care, if the deposit contains a care active, such as a moisturizer, and UV protection if it contains sun filters.

Thus, it would be desirable to obtain persistence of the effect produced (such as shaping, color, shine, matte appearance, and care), and/or durability of the cosmetic deposit, so that it offers resistance to factors of mechanical aggression such as rubbing, transfer by contact with another object, resistance to water, humidity, sweat, tears, the rain, and resistance to sebum and oils, and/or while remaining easy to remove when required.

In the case of make-up, this is particularly true for lipsticks, which require long-lasting color and shine, and non-transfer of the color; for nail varnishes, for which shine and durability of the film are desired; for foundations, eye shadow and powders, for which durability of the color is also sought, while maintaining matte appearance of the initial color for as long as possible despite the secretion of sebum and sweat (loss of matte appearance being due for the most part to variation of the color applied as a result of secretion of sebum and/or sweat, which may cause the skin to shine), as well as non-transfer.

In hairdressing, it is desirable to maintain a hairstyle throughout the day.

In cosmetics, the polymers conventionally used are often copolymers, in which the comonomers are bound to one another by covalent bonds.

It is customary to use polyurethanes as film-forming resin in a great many cosmetic formulations, for instance, in various make-up products such as nail varnishes, mascaras and eye-liners. To give satisfactory performance, it is desirable for the resin to not only have good film-forming properties, but also possess good properties of permanence, for example, resistance to removal from its substrate simply by washing with water.

In the case of make-up compositions, it would be desirable to have at one's disposal polymers of a different or identical chemical nature, readily soluble or dispersible in oils, cosmetic solvents and/or aqueous media, at variable concentration. It would also be desirable for these compositions, while providing increased persistence of the effects produced (such as color, shine, matte appearance, and/or care), to promote adhesion on keratinous materials, while facilitating make-up removal. This could provide colored compositions having increased constancy of color, for example, without deteriorating or becoming dull under the action of aggressive mechanical factors, water, sweat, tears, rain, sebum and oils, while preserving their other properties such as durability of color, shine, matte appearance and/or care.

In hairdressing, it is desirable for the composition to provide hairstyling that is long-lasting in the temperature and humidity conditions of everyday life.

To address these problems, it has been proposed that polymers capable of undergoing physical crosslinking, for example, polymers having groups that are able to form hydrogen bonds (H bonds), be used in cosmetic compositions.

Thus, International Patent Application No. WO 02/098377 describes a cosmetic composition for care, treatment, and make-up of keratinous materials comprising, in a physiologically acceptable medium, a linear, branched, cyclic or dendrimeric polymer having a polymer skeleton and a junction group capable of forming hydrogen bonds. The polymer skeletons can comprise poly(ethylene oxide) (PEO) units.

In addition, International Patent Application No. WO 03/032929 describes a hair treatment composition containing a polymer comprising at least two groups that are able to form hydrogen bonds.

Nail varnish compositions containing aqueous dispersions of aliphatic polyurethanes as film-forming resin were described in European Patent Application No. EP 418 469.

Nail varnishes containing an aqueous dispersion of a polyurethane and/or of a polyurethane copolymer were also described in European Patent Application No. EP 391 322.

Use of these resins does not, however, lead to the production of compositions with good cosmetic properties, for example, owing to lack of adhesion to the substrate.

Further, the passing of legislation that aims to reduce the content of volatile solvents, for example in cosmetic compositions, is leading formulators, such as of cosmetic compositions, to use aqueous media, or even water, as the preferred solvent for the formulation of compositions.

However, it is particularly difficult to use aqueous media, such as water or a medium containing water, as the vehicle for polymers while preserving the required properties of the compositions, for example, those that induce the added polymers. This may be the case in the field of hairdressing, where it is desirable for the polymers carried by the aqueous medium to provide sufficient styling, while ensuring a long-lasting effect.

It also proves difficult to use non-aqueous media, such as organic solvents and cosmetic oils, as vehicles for polymers, for example in the field of make-up products such as foundation or lipstick, as well as nail varnish.

The expression "use an aqueous or non-aqueous medium as vehicle for a polymer" means, in the context of the present disclosure, that the polymer is soluble and/or dispersible in the medium, at 25° C., at a concentration of at least 1 wt. %.

There is therefore a need for cosmetic compositions which can provide, after application on keratinous materials, deposits that combine persistence of the cosmetic and/or care effect, good adhesion of the composition to keratinous materials and/or quick and complete make-up removal, and which comprise polymers that can be dissolved or dispersed readily in the physiologically acceptable medium of the composition, such as in a medium containing water and which may also contain oil and/or a cosmetic organic solvent and such as in a medium based only on water.

The present disclosure therefore relates to cosmetic compositions, for example for care, cosmetic treatment and/or make-up of keratinous materials, that is able to overcome one or more of the drawbacks of the traditional formulations.

The inventors have found, surprisingly and unexpectedly, that a cosmetic composition comprising particular copolymers, having a poly(thio)urethane, poly(thio)urea or copoly(thio)urethane/(thio)urea polymer skeleton [designated by (thio)urethane/(thio)urea copolymers hereinafter] and comprising at least one junction group bound to the skeleton and capable of interacting with any partner junction group via the formation of at least 3 hydrogen bonds, can display good film-forming properties, and/or can make it possible to obtain robust films.

The disclosure thus also relates to cosmetic compositions comprising, in a physiologically acceptable medium, a copolymer having a (thio)urethane/(thio)urea polymer skeleton, resulting from the reaction:

- of at least one first monomer (a) having at least two polymerizable groups, which may be identical or different, chosen from —N=C=O and —N=C=S, and/or their activated or blocked forms;
- of at least one monomer (b1), having at least two polymerizable groups with a labile hydrogen, which may be identical or different, chosen from —OH, —SH, —NH$_2$ and —NHR, wherein R is a $C_1$-$C_6$ alkyl group; and
- at least one monomer (b2), different from monomer (b1), having at least two polymerizable groups with a labile hydrogen, which may be identical or different, chosen from —OH, —SH, —NH$_2$ and —NHR, wherein R is a $C_1$-$C_6$ alkyl group;
- wherein at least one of the monomers (a), (b1) and/or (b2) comprises at least one junction group (A), capable of forming at least 3 hydrogen bonds, such as at least 4 hydrogen bonds, for example, 4 hydrogen bonds.

The compositions according to the present disclosure may provide good adhesion to keratinous materials, and allow quick, complete and selective make-up removal. The compositions, in at least one embodiment, are not sticky.

In at least one embodiment, the compositions according to the disclosure can be film-forming, and can lead after application to filming of the compositions during drying.

According to at least one embodiment, the copolymers according to the present disclosure may be readily soluble or dispersible in water and organic solvents such as esters, e.g., alkyl esters such as alkyl acetates, alcohols, e.g., ethanol, carbon-containing and/or silicone oils, and mixtures thereof, for example, in the aqueous and/or oily and/or organic solvent media usually employed in cosmetics.

In at least one embodiment, the polymer according to the disclosure makes it possible to obtain a cosmetic composition that can be removed easily, relative to the compositions of the prior art, notably described in International Patent Application No. WO 02/98377. For example, in the case of hairdressing compositions, which are ideally easily removable by shampooing, the polymer according to the present disclosure may make such easy removal possible.

In at least one embodiment, compositions comprising polymers according to the present disclosure can have low viscosity, despite containing large amounts of polymers; this may also be true for the compositions in aqueous medium. These compositions still can exhibit good sprayability in formulations of the pump-spray, spray or aerosol type, and can permit a film-forming deposit to be obtained on the substrate.

According to at least one embodiment, the copolymers according to the present disclosure can be used for preparing aqueous dispersions or solutions that are very fluid and in addition can be stable without using additional surfactants, for example, when they also have ionizable functional groups.

"Polymer skeleton", also called -POL-, means, in the context of the present disclosure, a copolymer having at least three repeat units, which may be identical or different, bound covalently and able to be repeated several times in the skeleton. The copolymer can be linear, cyclic, branched, such as in star form, hyperbranched, dendrimeric or grafted, or crosslinked; it can be a random, alternating, block or other copolymer, for example, a block copolymer.

"Having at least three repeat units" means, according to the present disclosure, a constituent unit of a polymer resulting from the copolymerization of at least three, identical or different, monomeric or oligomeric units.

"Junction group", also called A, means in the context of the disclosure any entity or functional group having hydrogen-bond donor or acceptor groups, and capable of establishing at least 3 hydrogen bonds, such as at least 4 hydrogen bonds, for example, 4 hydrogen bonds, with a partner junction group, of identical or different chemical nature.

The junction groups (A) can be lateral to the polymer skeleton (in side branches), and/or localized at the ends of the polymer skeleton, and/or integrated in the chain forming the polymer skeleton. Their distribution in the chain can be random or controlled.

"Partner junction group" means, in the context of the present disclosure, any junction group of a copolymer according to the invention that can establish H bonds with at least one junction group of a same or of another copolymer according to the disclosure. The junction groups can be of identical or different chemical nature. If they are identical, they can then establish hydrogen bonds between them and are then called self-complementary junction groups. If they are different, they can be chosen in such a way that they are complementary with respect to H interactions.

The use of such copolymers in a cosmetic composition can lead, after application of this composition on keratinous materials, to the formation of a supramolecular polymer.

"Supramolecular polymer" means, in the context of the present disclosure, a polymer chain or network formed from the assembly of a copolymer as disclosed herein with at least one other copolymer according to the disclosure, which may be identical or different, each assembly comprising at least one pair of paired junction groups, which may be identical or different.

"Pair of paired junction groups" means, in the context of the present disclosure, two junction groups, each of which can be carried or not by one and the same copolymer according to the disclosure, the two groups being joined together via at least 3 hydrogen bonds, such as at least 4 hydrogen bonds, for example, 4 hydrogen bonds. The copolymers of the present disclosure can combine by pairing of their junction groups with a junction group that is chemically identical (or self-complementary) or chemically different.

Thus, the supramolecular polymer may have physical crosslinking points that are provided by the hydrogen bonds between these pairs of junction groups. The physical crosslinking may ensure that the cosmetic and/or care effect will be maintained for a long time, in a similar manner to chemical crosslinking, while permitting reversibility, for example, the possibility of removing the deposit completely either with a specific make-up remover, or by means of temperature, or by any other means, which is not possible in the case of chemical crosslinking.

Copolymers according to the present disclosure, having at least one junction group, in a cosmetic composition can lead, after application of the composition on keratinous materials, either to the formation of a supramolecular copolymer in the form of a physically crosslinked three-dimensional network, such as in the form of a film, and having very good mechanical resistance, or to the formation of a supramolecular copolymer in the form of a long polymer chain, generally of high molecular weight, resulting from the physical linking of the copolymers of the present disclosure.

Multifunctional copolymers (possessing several junction groups) may offer a greater probability of crosslinking, which means that a smaller amount of polymer can be used for the same efficiency of crosslinking, and possibly enhance the mechanical properties of the products.

When the copolymer is formulated with volatile solvents, it is possible to obtain filming of the composition during drying, when this is permitted by the structure of the copolymer.

"Filming" means, in the context of the present disclosure, the formation of a continuous deposit in the form of films and possessing mechanical properties that are similar to those of high molecular weight copolymers or chemically crosslinked networks.

"Carbon-containing divalent radical" means, according to the present disclosure, radicals comprising atoms of carbon and hydrogen, and optionally at least one heteroatom; for example, the carbon-containing divalent radicals are aliphatic divalent radicals that are saturated (alkyl) or unsaturated, linear and branched, cyclic and non-cyclic, aromatic and non-aromatic, having 1 to 40 carbon atoms, substituted or unsubstituted, and can optionally have at least one heteroatom chosen from: O, S, N, P, Si and F, for example O, S and N and combinations of these radicals.

General Structure of the Copolymers According to the Present Disclosure

The copolymers according to the disclosure result from the reaction of at least one monomer (a), of at least one monomer (b1) and of at least one monomer (b2), with at least one of these monomers having at least one junction group (A).

In at least one embodiment, at least one of the monomers (a), (b1) and/or (b2) comprises at least two junction groups (A), capable of forming at least 3 hydrogen bonds, such as at least 4 hydrogen bonds, for example, 4 hydrogen bonds.

Additionally, the copolymers according to the disclosure can be represented schematically by the following general formula: POL-(A)$_i$ wherein:
POL is the poly(thio)urethane/(thio)urea polymer skeleton,
A is a junction group bound to the polymer skeleton and capable of establishing hydrogen bonds with at least one partner junction group, of identical or different chemical nature, with each pairing of a junction group involving at least 3 hydrogen bonds, such as at least 4 hydrogen bonds, for example, 4 hydrogen bonds, and
i is an integer greater than or equal to 1, for example, greater than or equal to 2.

In at least one embodiment, the copolymers according to the present disclosure can have at least one of the following structures:
1. linear copolymer functionalized at α, ω with junction groups (A);
2. linear copolymer with at least two junction groups, located in the chain and/or at one or at both ends and/or in branchings;
3. branched copolymer with junction groups integrated in the chain and/or in a branching and/or at one or at both ends.

Copolymers according to the present disclosure can have just one of these structures, or a mixture of these structures, in all proportions.

General Definition of the Junction Groups A

According to the present disclosure, a junction group A is a chemical group that is capable of forming at least 3 hydrogen bonds, such as at least 4 hydrogen bonds, for example, 4 hydrogen bonds, and in at least one embodiment, comprises at least 3 heteroatoms, which may be identical or different, for example, 4 heteroatoms, which may be identical or different, chosen from O, N, S, P and F, for example, chosen from O, S and N.

These junction groups can comprise for example at least 3 functional groups, and in at least one embodiment, at least 4 functional groups, chosen from:

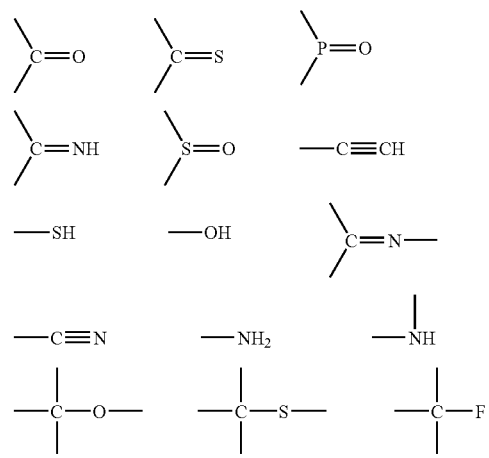

These functional groups can be placed in two categories:
H-bond-donor functional groups such as the groups:

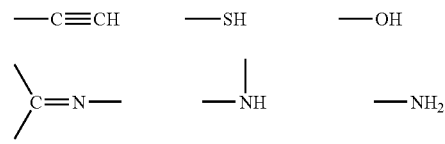

and H-bond-acceptor functional groups such as the groups:

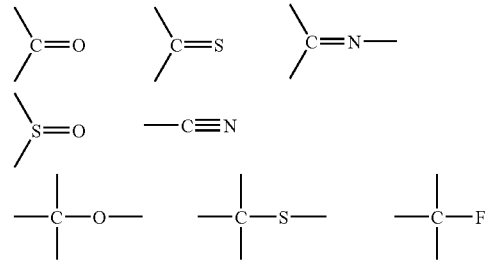

The junction groups A can form a basic structural element having at least 3 groups, such as at least 4 functional groups, for example, 4 functional groups, capable of establishing hydrogen bonds. The basic structural elements capable of establishing at least 3 or 4 hydrogen bonds can be represented schematically as follows:

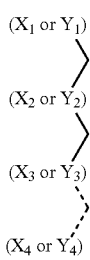

where $X_i$ (where i is a natural integer) is an H-bond-acceptor functional group and $Y_i$ is an H-bond-donor functional group.

Thus, each structural element may be able to establish hydrogen bonds with at least one partner structural element, identical (for example, self-complementary) or different, in such a way that each pairing of two partner structural elements takes place by formation of at least 3 hydrogen bonds, such as at least 4 hydrogen bonds, for example, 4 hydrogen bonds.

A proton acceptor X will pair with a proton donor Y.

There are several possibilities, for example:

Pairing of:

XXXX with YYYY;

XXXY with YYYX;

XXYX with YYXY;

XYYX with YXXY;

XXYY with YYXX self-complementary or not;

XYXY with YXYX self-complementary or not.

In at least one embodiment, the junction groups A can establish 4 hydrogen bonds with an identical (or self-complementary) partner group including 2 donor bonds (for example NH) and 2 acceptor bonds (for example CO and —C=N—).

In at least one embodiment, the junction groups have rings with 5 or 6 atoms, (aromatic rings or unsaturated heterocycles) optionally constituted of C and/or N atoms and with conjugated double bonds for stabilizing and directing the H bonds.

In at least one embodiment, the junction groups are inserted in rings with 6 atoms comprising C and/or N atoms and with conjugated double bonds for stabilizing and directing the H bonds.

According to at least one embodiment, the junction groups (A) capable of forming 3 or 4 H bonds may be chosen from the following families, it being understood that all the tautomeric forms are included:

(i) aminopyrimidones of formula:

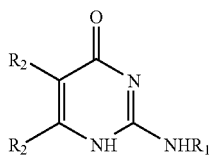

(ii) ureidopyrimidones of formula:

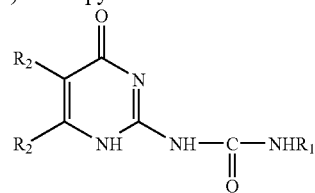

(iii) acylaminopyridines and including:

monoacylaminopyridines of structure:

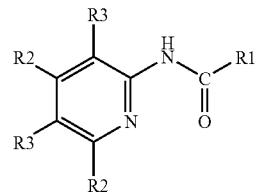

di(acylamino)pyridines such as 2,6-di(acylamino)pyridines of structure:

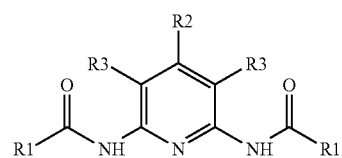

(iv) aminopyrimidines, such as:

aminopyrimidine compounds:

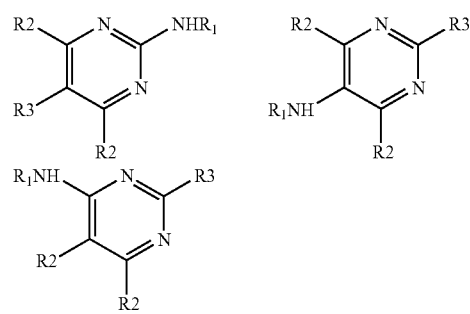

diaminopyrimidine compounds of structure:

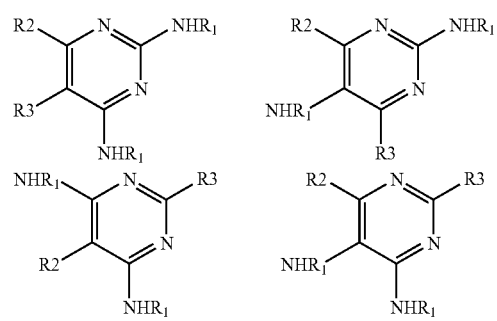

triaminopyrimidine compounds;

(v) ureidotriazines, such as the mono-, di- and triureidotriazines, and ureidoaminotriazines of structure:

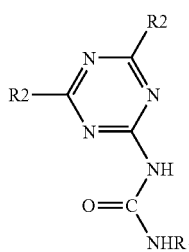

(vi) (acylamino)triazines, such as the mono-, di- and triacylaminotriazines, optionally amino (mono-, di- or triamino) and including:
di(acylamino)triazines of structure:

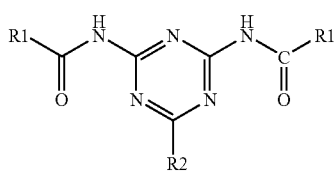

acylamino, aminotriazines (mono- or diacylamino, and mono- or diamino) and the compounds of the structure:

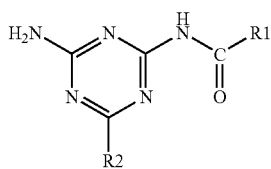

acylaminotriazines of structure:

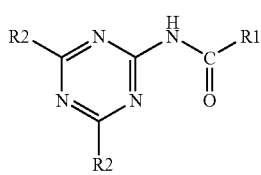

triacylaminotriazines,
(vii) aminotriazines such as:
monoaminotriazines,
2,6-diamino-s-triazines of structure:

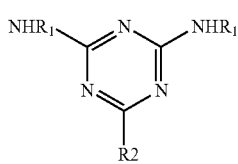

triamino-s-triazine compounds of structure:

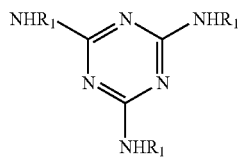

(viii) acylaminotriazoles of structure:

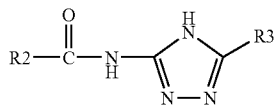

(ix) compounds of the urazoylbenzoic acid family of structure:

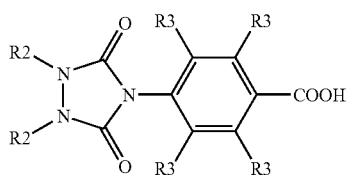

(x) phthalhydrazides of structure:

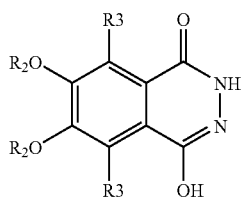

(xi) uracils of structure:

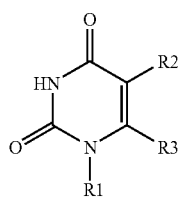

(xii) thymines of structure:

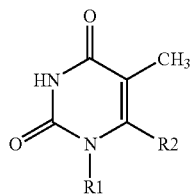

(xiii) succinimides of structure:

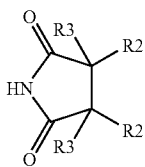

(xiv) glutarimides of structure:

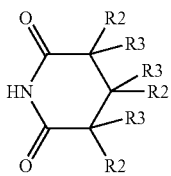

(xv) compounds of the cyanuric acid family of structure:

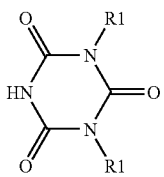

(xvi) maleimides:

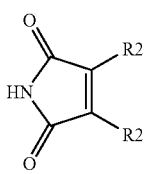

(xvii) compounds of the barbituric acid family of structure:

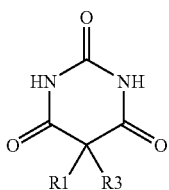

(xviii) compounds of structure:

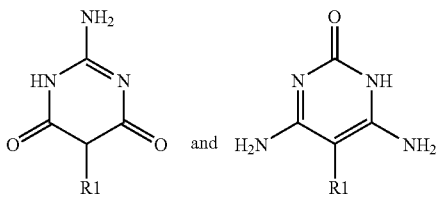

(xix) compounds of trimellitic family, of formula:

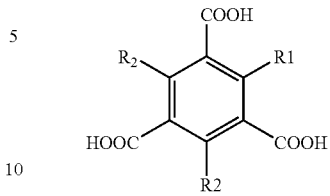

(xx) ureidopyridines, such as mono- or diureidopyridines, and those of formula:

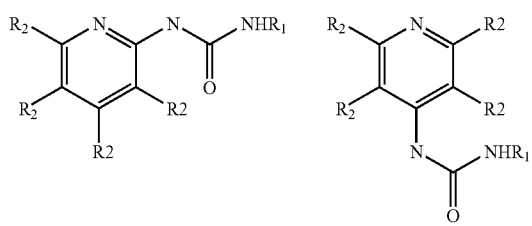

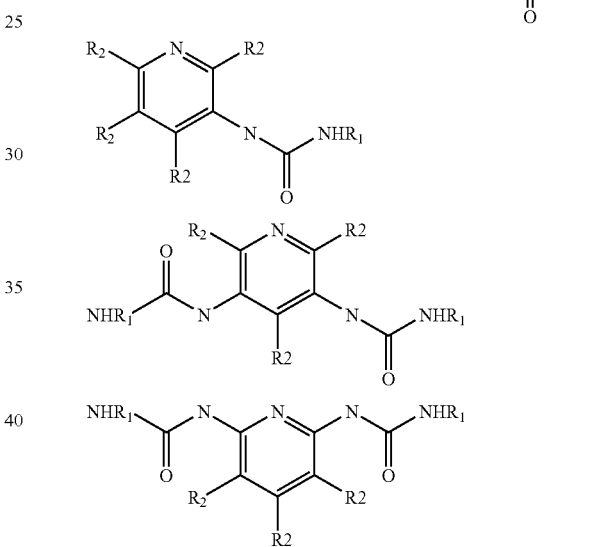

(xxi) carbamoylpyridines of formula:

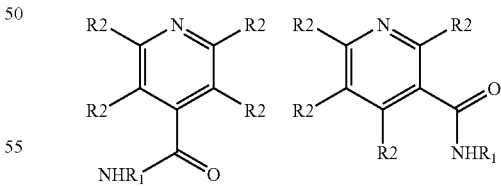

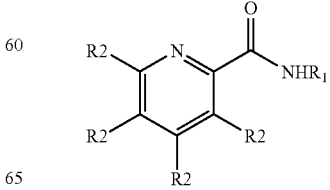

(xxii) adenines of formula:

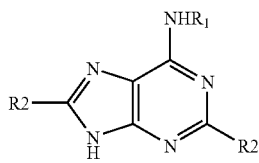

(xxiii) guanines of formula:

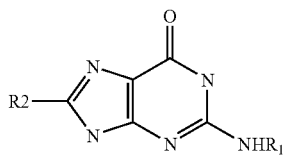

(xxiv) cytidines of formula:

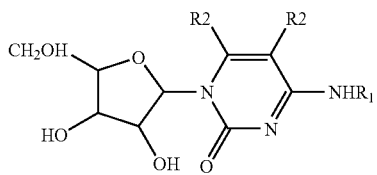

In all these formulae, the radicals have the following meanings:
(a) the radicals R1, which may be identical or different, are chosen from hydrogen atoms, halogens, monovalent linear, branched and cyclic, saturated and unsaturated, optionally aromatic, $C_1$-$C_{6000}$ carbon-based groups (for example, alkyls), which may contain at least one heteroatom such as O, S, N, P, Cl, Br, F; and from combinations thereof.

In at least one embodiment, radical R1 may be chosen from $C_4$-$C_{12}$ cycloalkyl groups; linear and branched $C_1$-$C_{30}$ alkyl groups and $C_4$-$C_{12}$ aryl groups; optionally substituted with an amino, ester and/or hydroxyl function.

In at least one embodiment, R1 is chosen from: —$C_4H_9$, -phenyl, 1,4-nitrophenyl, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethyl-hexylene), 1,7-(3,7-dimethyloctylene), isophorone, 4,4'-methylenebiscyclohexylene, tolylene, 2-methyl-1,3-phenylene, 4-methyl-1,3-phenylene, and 4,4-biphenylenemethylene, and in at least one further embodiment, R1 is chosen from isophorone, —$(CH_2)_2$—, —$(CH_2)_6$—, —$CH_2CH(CH_3)$—$CH_2$—$C(CH_3)_2$—$CH_2$—$CH_2$, 4,4'-methylenebis(cyclohexylene) and 2-methyl-1,3-phenylene group.
(b) the radicals R2, which may be identical or different within the same formula, are chosen from hydrogen atoms, halogens (such as, —Br, —Cl, —F), —OH, —N(R)$_2$ (wherein R is chosen from hydrogen atoms and linear and branched $C_1$-$C_{12}$ alkyl groups, for example, a $C_1$-$C_4$ alkyl radical and such as a methyl or ethyl radical); monovalent linear, branched and cyclic, saturated and unsaturated, optionally aromatic, $C_1$-$C_{6000}$ hydrocarbon-based groups, which may contain at least one heteroatom such as O, S, N, P or F; and from combinations thereof.

In at least one embodiment, the radicals R2 may be chosen from:
hydrogen atoms;
CN groups;
NH$_2$ groups;
$C_1$-$C_{30}$ alkyl groups;
$C_4$-$C_{12}$ cycloalkyl groups;
$C_4$-$C_{12}$ aryl groups;
($C_4$-$C_{12}$)aryl($C_1$-$C_{30}$)alkyl groups;
$C_1$-$C_4$ alkoxy groups;
arylalkoxy groups, for example, ($C_1$-$C_4$) arylalkoxy groups;
$C_4$-$C_{12}$ heterocycles;
thioalkoxy groups,
sulfoxy groups,
or mixtures thereof, these groups being optionally substituted with an amino, ester and/or hydroxyl function.

In at least one embodiment, R2 is chosen from H, CH$_3$, $C_{13}H_{27}$, $C_7H_{15}$ and phenyl.
(c) the radicals R3, which may be identical or different within the same formula, are chosen from hydrogen atoms, monovalent linear, branched and cyclic, saturated and unsaturated, optionally aromatic, $C_1$-$C_{6000}$ hydrocarbon-based groups, which may contain at least one heteroatom such as O, S, N, P or F; and from combinations thereof; In at least one embodiment, the radical R3 may be chosen from $C_4$-$C_{12}$ cycloalkyl groups; linear and branched $C_1$-$C_{30}$ alkyl group; and $C_4$-$C_{12}$ aryl groups; optionally substituted with at least one function chosen from amino, ester and hydroxyl function.

In all these formulae, it is clearly understood that at least one, for example one or two, of the groups R1 and/or R2 is the point of attachment of the junction group A to the polymer backbone POL.

In at least one embodiment, the point of attachment is borne by R1 and/or R2 and in at least one further embodiment, when there is only one point of attachment, it is borne by the group R1.

In at least one embodiment, the junction groups (A) may be chosen from:
(a) the complementary and identical, i.e. self-complementary, junction groups (A) and, for example:
aminopyrimidones, ureidopyrimidones,
compounds of the trimellitic acid family, or from urazoylbenzoic acid,
acylaminopyridines, ureidopyridines, carbamoylpyridines,
acylaminotriazines, ureidotriazines and for example, ureidoaminotriazines, diaminotriazines,
acylaminotriazoles,
phthalhydrazides,
compounds of formulae:

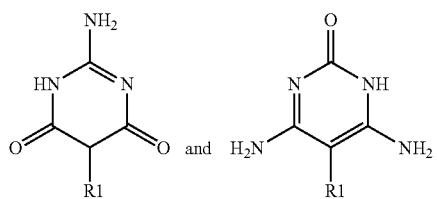

wherein R1 is chosen from H and linear, branched and cyclic, saturated and unsaturated, optionally aromatic, $C_1$-$C_{6000}$ hydrocarbon-based groups, which may contain at least one heteroatom such as O, S, N, P or F; and (b) the complementary but different junction groups (A) and for example:
  adenine, which is complementary to guanine,
  cytidine, which is complementary to thymine,
  triamino-s-triazine, which is complementary to uracil or succinimide or glutarimide or cyanuric acid or thymine or maleimide or (di)aminopyrimidine or barbituric acid;
  acylaminoamino-s-triazine, which is complementary to uracil or succinimide or glutarimide or cyanuric acid or thymine or maleimide or (di)aminopyrimidine or barbituric acid.

In at least one embodiment, the junction groups A are chosen from the groups which are capable of establishing at least three H bonds with each other (self-complementary), such as at least four H bonds. Among these groups, non-limiting mention may be made of:
  ureidopyrimidones;
  ureidopyridines, carbamoylpyridines;
  acylamino-s-triazines such as acyldiamino-s-triazines;
  ureidotriazines;
  phthal hydrazides;
  compounds of formulae:

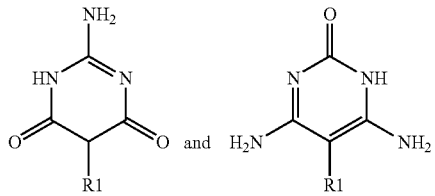

wherein the radicals R1, R2 and R3 are as defined above.

In at least one embodiment, junction groups capable of establishing at least three H bonds with each other include:
  2-ureidopyrimidone;
  6-methyl-2-ureidopyrimidone;
  diacyl-2,6-diamino-s-triazine;
  ureido-s-triazine;
  compounds of formulae:

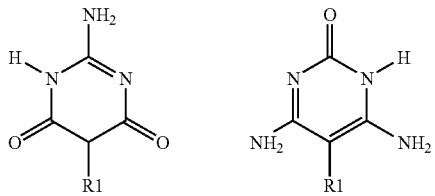

wherein the radicals R1, R2 and R3 are as defined above.

As will be pointed out later, in at least one embodiment of the invention, at least one of the junction groups A can bear at least one ionizable group as defined below.

According to at least one embodiment, at least one of the radicals R1, R2 and/or R3 of the above compounds can bear an ionizable group as defined below.

In at least one embodiment, the copolymers according to the disclosure bear at least two junction groups (A), such as at least four groups and, for example, four or six junction groups, per chain of copolymers.

In at least one embodiment, the monomer bearing the junction group or groups (A) is monomer (a) and/or (b2), for example, monomer (a).

As mentioned above, the copolymer according to the disclosure results from the reaction:
  of at least one monomer (a) having at least two polymerizable groups, which may be identical or different, chosen from —N=C=O and —N=C=S, or their activated or blocked forms;
  of at least one monomer (b1), having at least two polymerizable groups with a labile hydrogen, which may be identical or different, chosen from —OH, —SH, —NH$_2$ and —NHR, wherein R is a $C_1$-$C_6$ alkyl group; and
  of at least one monomer (b2), different from monomer (b1), having at least two polymerizable groups with a labile hydrogen, which may be identical or different, chosen from —OH, —SH, —NH$_2$ and —NHR, wherein R is a $C_1$-$C_6$ alkyl group;
  wherein at least one of the monomers (a), (b1) and/or (b2) comprising at least one junction group (A), capable of forming at least 3, such as at least 4 hydrogen bonds, for example, 4 hydrogen bonds.

Monomer (a)

Monomer (a) can therefore be chosen from compounds of formula Y=C=N—$R^a$—N=C=Y' wherein Y and Y', which may be identical or different, can be chosen from O and S. In at least one embodiment, Y=Y' and in a further embodiment, Y=Y'=O.

When it is in activated or blocked form, monomer (a) can also be of formula B—C(O)—NH—$R^a$—NH—C(O)—B' as described in "Comprehensive Polymer Science", Vol. 5: step polymerization p. 421, Pergamon Press (1989).

Thus, B and B' can be chosen, independently of one another, from:

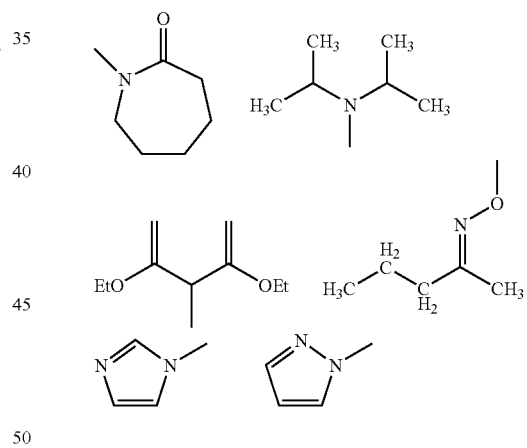

In at least one embodiment, a first family (a1) of monomers (a) is that wherein $R^a$ chosen from aliphatic divalent radicals, saturated and unsaturated, linear and branched, cyclic and non-cyclic, aromatic and non-aromatic, and which have 1 to 40 carbon atoms, optionally comprising at least one heteroatom chosen from O, S and/or N, and/or optionally substituted with at least one fluorine atom and/or hydroxyl radical, and mixtures thereof.

The radical $R^a$ can, for example, be chosen from linear and branched $C_1$-$C_{30}$ alkyl group, a $C_4$-$C_{12}$ cycloalkyl group and a $C_4$-$C_{12}$ aryl group; optionally substituted with an ester and/or amide function.

$R^a$ can for example be chosen from:
  —(CH$_2$)$_c$—, —(CRH)$_c$ and —(CRR')$_c$ wherein R and R', which may be identical or different, are linear and branched $C_1$-$C_{30}$ alkyl groups and c is an integer from 1 to 20, for example, from 1 to 12;

and alternatively of structure:

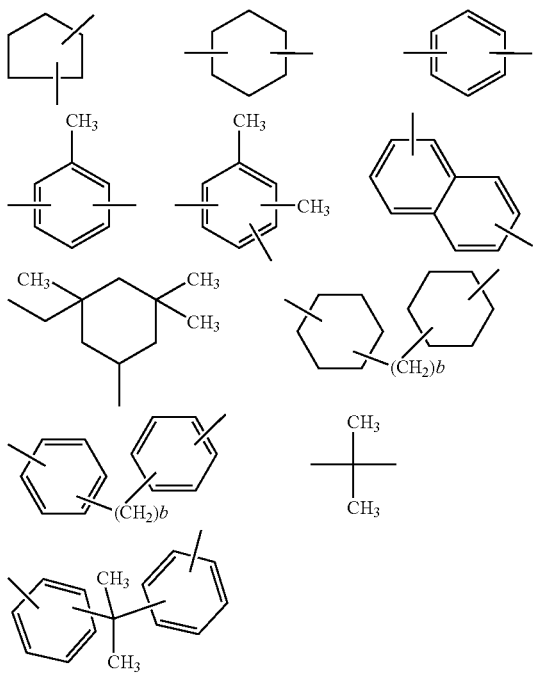

wherein b is an integer ranging from 0 to 3;
as well as all combinations of these structures.

In at least one embodiment, the divalent radicals $R^a$ may be chosen from: 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), 4,4'-methylene-bis(cyclohexyl), 1,4-cyclohexylene, 2,4-tolylene, 2,6-tolylene; 1,5-naphthylene, 4,4'-methylene-bis(phenyl), and tetramethyl xylylene, the divalent radical derived from isophorone.

In at least one embodiment, monomers (a) can be chosen from the following compounds:
1,4-diisocyanatobutane,
1,6-hexamethylenediisocyanate or 1,6-diisocyanatohexane,
1,5-diisocyanato-2-methyl-pentane,
1,4-diisocyanato-4-methyl-pentane,
1,6-diisocyanato-2,2,4-trimethylhexane,
1,6-diisocyanato-2,4,4-trimethylhexane,
1,5-diisocyanato-5-methylhexane,
3(4)-isocyanatomethyl-1-methylcyclohexyl-isocyanate,
1,6-diisocyanato-6-methyl-heptane,
1,5-diisocyanato-2,2,5-trimethylhexane,
1,7-diisocyanato-3,7-dimethyloctane,
1-isocyanato-1,2,2-trimethyl-3-(2-isocyanato-ethyl)-cyclopentane,
1-isocyanato-n-butyl-3-(4-isocyanatobut-1-yl)-cyclopentane,
1-isocyanato-1,2-dimethyl-3-ethyl-3-isocyanatomethyl-cyclopentane,
1-isocyanato-1-methyl-4-(4-isocyanatobut-2-yl)-cyclohexane,
1-isocyanato-1,4-dimethyl-4-isocyanatomethyl-cyclohexane,
1-isocyanato-1,3-dimethyl-3-isocyanatomethyl-cyclohexane,
1,3-bis(isocyanatomethyl)cyclohexane,
isophorone diisocyanate,
4,4'-methylene-bis(cyclohexyl isocyanate)
1,4-diphenylene diisocyanate; tolylene 2,4-diisocyanate; tolylene 2,6-diisocyanate,
1,3-bis(isocyanatomethyl)benzene,
4,4'-methylene-bis(phenyl isocyanate),
naphthalene diisocyanate, and
tetramethyl-1,3-xylylenediisocyanate.

These diisocyanates can be used alone or as a mixture of two or more diisocyanates.

In at least one embodiment, a second family (a2) of monomers (a) is that wherein the divalent radical $R^a$ is a polymer radical, for example of the homopolymer or copolymer type, chosen for example from:
the ethylenic copolymers such as the polyolefins bearing units chosen from 1,2-butadiene; 1,4-butadiene; isoprene; ethylene; propylene; 1,2-butylene; 1,4-butylene; isobutylene; the (meth)acrylic copolymers; the (meth)acrylamide copolymers; the vinylic copolymers; the allylic copolymers and mixtures thereof.

Thus, the following are non-limiting examples may be used according to at least one embodiment of the disclosure: vinyl/(meth)acrylate, vinyl/(meth)acrylamide, vinyl/(meth)acrylate/methacrylamide, olefinic/vinylic and (meth)acrylate/(meth)acrylamide copolymers;
the polyethers, perfluorinated or not, such as polyethylene oxide, polypropylene oxide, and their polyethylene oxide/polypropylene oxide copolymers, the polytetramethylene oxides and perfluoropolyethers, the polythioethers;
polyesters and for example polyesters based on adipic acid or terephthalic acid, polycaprolactone, poly(2-methyl-1,3-propylene-adipate), poly-(2-methyl-1,3-propylene)-glutarate, sulphonic polyesters;
polylactides;
polyamides;
polyoxazolines such as poly(2-methyloxazoline) or poly (2-ethyloxazoline);
siloxane copolymers, for example polysiloxanes comprising —Si($R^4$)($R^5$)O— units, where ($R^4$) and ($R^5$), which may be identical or different, are hydrogen atoms or linear and branched, cyclic and non-cyclic, saturated and unsaturated, and aromatic, carbon-containing radicals, such as a $C_1$-$C_{12}$ alkyl optionally bearing at least one heteroatom, for example 1 to 5 heteroatoms, which may be identical or different, chosen from O, N, S, P, F and Si, for example, chosen from O, N and S, and such as the polydimethylsiloxanes (PDMS), and the poly(methylphenylsiloxanes);
copolymers of these various types of polymers, for example the polysiloxane/poly(ethylene oxide) copolymers;
polyacetals;
polycarbonates, perfluorinated or not;
and mixtures thereof.

In at least one embodiment, when $R^a$ is a polymer radical, it has a weight-average molecular weight (Mw) ranging from 500 to 30,000, for example from 700 to 25,000 or from 800 to 15,000.

In at least one embodiment, $R^a$ can be chosen from functional polymers of the type:
polyesters, such as those based on adipic acid and/or terephthalic acid, poly(2-methyl-1,3-propylene-adipate) and poly(2-methyl-1,3-propylene)-glutarate;
polyethers and including poly(tetramethylene oxide);

siloxane copolymers; and
poly(ethylene-butylene)s and polybutadienes.

When $R^a$ corresponds to a mixture of different polymers, the percentage of the different polymers can be selected by a person skilled in the art in relation to the required properties.

In at least one embodiment, the monomers (a) are of type (a1), alone or mixtures thereof. However, in at least one embodiment, it is also possible to have a mixture of monomers (a1), alone or mixed, and of monomers (a2), alone or mixed.

When the monomer (a) has at least one junction group (A), it can be of formula:

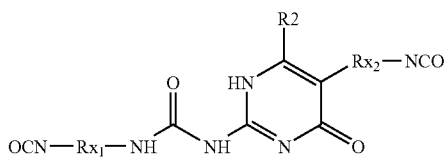

wherein $Rx_1$ and $Rx_2$, which may be identical or different, are a divalent carbon-containing radicals chosen from linear and branched $C_1$-$C_{30}$ alkyl groups, $C_4$-$C_{12}$ cycloalkyl groups and $C_4$-$C_{12}$ aryl groups; optionally comprising 1 to 8 heteroatoms chosen from O, N, S, F, Si and P; optionally substituted with an ester or amide function or with a $C_1$-$C_{12}$ alkyl radical, or a mixture of these groups;

R2 being as defined above for the junction group (A).

In at least one embodiment, monomer (a) can be of formula:

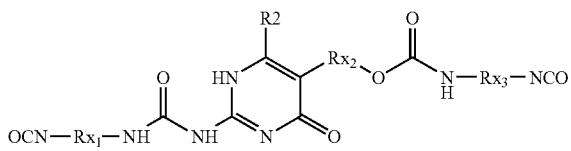

wherein $Rx_1$, $Rx_2$, and $Rx_3$, which may be identical or different, are divalent carbon-containing radicals chosen from linear and branched $C_1$-$C_{30}$ alkyl groups, $C_4$-$C_{12}$ cycloalkyl groups, and $C_4$-$C_{12}$ aryl groups; or mixtures thereof;

and R2 is a $C_1$-$C_{32}$ alkyl radical.

According to at least one embodiment, monomer (a) can be of formula:

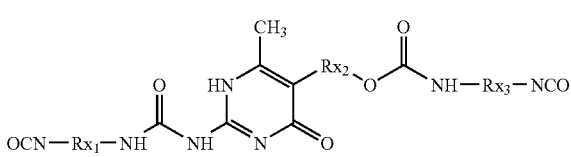

wherein the radicals $Rx_1$, $Rx_2$ and $Rx_3$, independently of one another, can, in at least one embodiment, be chosen from the following radicals: methylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), 4,4'-methylene-biscyclohexylene, 2-methyl-1,3-phenylene; 4-methyl-1,3-phenylene, 4,4'-biphenylenemethylene, 1,2-tolylene, 1,4-tolylene, 2,4-tolylene, 2,6-tolylene, 1,5-naphthylene, 4,4'-methylene-bis (phenyl), and tetramethyl xylylene, the divalent radical derived from isophorone.

In at least one embodiment, $Rx_1$, $Rx_2$ and $Rx_3$ are chosen from, independently of one another, —(CH$_2$)$_2$—, —(CH$_2$)$_6$—, —CH$_2$CH(CH$_3$)CH$_2$C(CH$_3$)(CH$_3$)CH$_2$CH$_2$—, and isophorone-radicals; and in at least one further embodiment, $Rx_1$, and $Rx_3$ are isophorone- radicals and $Rx_2$ is —(CH$_2$)$_2$—, which leads to the following monomer (a):

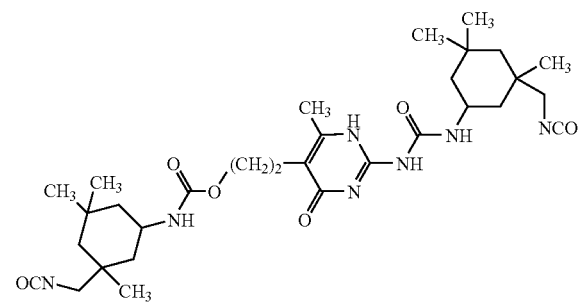

Monomers (b): HX—$R^b$—X'H

The copolymer according to the disclosure may also comprise at least two monomers (b1) and (b2), different from one another, and both comprising at least two polymerizable groups, which may be identical or different, chosen from —OH, —SH, —NH$_2$ and —NHR wherein R=$C_1$-$C_6$ alkyl.

In at least one embodiment, in (b1), X and/or X'=O and in at least one further embodiment, X=X'=O.

The divalent radical $R^{b1}$, in at least one embodiment, is a divalent polymer radical, such as of the homopolymer or copolymer type, for example chosen from the dithiol functional copolymers, diamines, diols, aminoalcohol, the alcohol, amine and/or thiol functions being carried at the ends of the chain or along the skeleton; as a polymer radical, non-limiting examples include the following types of radicals:

polyethers, perfluorinated or not, such as poly(ethylene oxide), poly(propylene oxide), and their poly(ethylene oxide)/poly(propylene oxide) copolymers, the poly(tetramethylene oxide)s, the perfluoropolyethers and the polythioethers;

polylactides;

polyesters, including those based on adipic acid or terephthalic acid, such as polycaprolactone; poly(2-methyl-1, 3-propylene-adipate), poly-(2-methyl-1,3-propylene)-glutarate, the sulphonic polyesters;

polyamides;

polyoxazolines such as poly(2-methyloxazoline), poly(2-ethyloxazoline);

siloxane copolymers, for example the polysiloxanes comprising —Si($R^4$)($R^5$)O— units, where ($R^4$) and ($R^5$), which may be identical or different, are chosen from hydrogen atoms and linear and branched, cyclic and non-cyclic, saturated and unsaturated, and aromatic, carbon-containing radicals, such as $C_1$-$C_{12}$ alkyls which can optionally have at least one heteroatom, for example 1 to 5 heteroatoms, which may be identical or different, chosen from: O, N, S, P, F and Si, for example, chosen from O, N and S, and such as polydimethylsiloxanes (PDMS), and poly(methylphenylsiloxanes);

polyacetals;

ethylenic copolymers including (meth)acrylic copolymers, (meth)acrylamide copolymers, vinylic copolymers, allylic copolymers; vinyl/(meth)acrylate, vinyl/(meth)acrylamide, vinyl/(meth)acrylate/(meth) acrylamide, olefinic/vinylic and (meth)acrylate/(meth)

acrylamide copolymers are used in at least one embodiment of the present disclosure;

polyolefins bearing units chosen from 1,2-butadiene, 1,4-butadiene, isoprene, ethylene, propylene, 1,2-butylene, 1,4-butylene, and isobutylene;

polycarbonates, perfluorinated or not;

copolymers of these various types of polymers, for example polysiloxane/poly(ethylene oxide) copolymers;

and mixtures thereof.

Monomer (b1), in at least one embodiment, has a weight-average molecular weight (Mw) ranging from 500 to 30,000, for example, from 700 to 25,000 or from 800 to 15,000.

When $R^{b1}$ corresponds to a mixture of different polymers, the percentage of the different polymers can be chosen by a person skilled in the art in relation to the required properties.

In at least one embodiment, $R^{b1}$ can be chosen from functional polymers such as:

polyesters, such as those based on adipic acid and/or of terephthalic acid, and for example, poly(2-methyl-1,3-propylene-adipate) and poly-(2-methyl-1,3-propylene)-glutarate;

polyethers, such as poly(tetramethylene oxide)s;

siloxane copolymers; and poly(ethylene-butylene)s and polybutadienes.

The monomer (b2) can therefore be of formula HX—$R^{b2}$—X'H, with X and X', which may be identical or different, chosen from O, S, NH and NR, wherein R is a $C_1$-$C_6$ alkyl group.

In at least one embodiment, in monomer (b2), X and/or X'=O and in a further embodiment, X=X'=O.

The divalent radical $R^{b2}$, in at least one embodiment, is chosen from divalent carbon-containing radicals having from 1 to 40 carbon atoms, linear and branched, cyclic and non-cyclic, saturated and unsaturated, aromatic and non-aromatic, optionally with at least one heteroatom chosen from O, S, P and N, and/or optionally substituted with at least one atom of fluorine and/or silicon.

The heteroatom or heteroatoms, when they are present, can be inserted in the chain of the radical, or alternatively the radical can be substituted with at least one group containing them, such as hydroxyl or amino groups ($NH_2$, NHR' or NR'R" wherein R' and R", which may be identical or different, are chosen from linear and branched $C_1$-$C_{22}$ alkyls, optionally containing 1 to 12 heteroatoms chosen from O, N, S, F, Si and P, for example, methyl or ethyl).

According to at least one embodiment, $R^{b2}$ can comprise:

an alkylene radical having 1 to 40 carbon atoms or a cycloalkylene radical having 3 to 16 carbon atoms, optionally substituted with a $C_1$-$C_{12}$ alkyl radical optionally containing 1 to 8 heteroatoms chosen from O, N, S, F, Si and P such as methylene, ethylene, propylene, n-butylene, isobutylene, tert-butylene, n-hexylene, n-octylene, n-dodecylene, n-octadecylene, n-tetradecylene, n-docosanylene; ethyl-2-hexylene, cyclohexylene, cyclohexylmethylene, isophorone;

a $C_1$-$C_{30}$ arylene radical such as a —$C_6H_4$-(ortho, meta or para) phenylene radical, optionally substituted with a $C_1$-$C_{12}$ alkyl radical optionally containing 1 to 25 heteroatoms chosen from O, N, S, F, Si and P;

a benzylene radical —$C_6H_4$—$CH_2$— optionally substituted with a $C_1$-$C_{12}$ alkyl radical optionally containing 1 to 8 heteroatoms chosen from O, N, S, F, Si and P;

a $C_1$-$C_{30}$, such as $C_2$-$C_{12}$, alkarylene or aralkylene radical, a radical of formula: —O—CO—O—, —CO—O—, —OCO—, —O—CO—NH—, anhydride, —NH—CO—NH—, —NHCO;

a radical —Si($R^4$)($R^5$)O— wherein $R^4$ and $R^5$, which may be identical or different, are chosen from hydrogen atoms and linear and branched, cyclic and non-cyclic, saturated and unsaturated, and aromatic, hydrocarbon radicals, such as $C_1$-$C_{12}$ alkyls which can optionally contain at least one heteroatom, such as 1 to 5 heteroatoms, which may be identical or different, chosen from O, N, S, P, F and Si, for example, chosen from O, N and S;

an oxyalkylene or aminoalkylene radical, for example, an alkylene oxide radical of formula —(R"O)$_y$R$^{iv}$ wherein R" is chosen from linear and branched $C_2$-$C_4$ alkyls, R$^{iv}$ is chosen from hydrogen and linear and branched $C_1$ to $C_{30}$ alkyl radicals and y is a number ranging from 1 to 500 inclusive, such as from 1 to 250;

a mixture of these radicals.

In at least one embodiment, $R^{b2}$ is chosen from:

an alkylene radical having from 1 to 40 carbon atoms or a cycloalkylene radical having from 3 to 16 carbon atoms, optionally substituted with a $C_1$-$C_{12}$ alkyl radical optionally containing 1 to 8 heteroatoms chosen from O, N, S, F, Si and P such as methylene, ethylene, propylene, n-butylene, n-pentylene, isobutylene, tert-butylene, n-hexylene, n-octylene, n-dodecylene, n-octadecylene, n-tetradecylene, n-docosanylene, ethyl-2-hexylene, cyclohexylene, cyclohexylmethylene, isophorone;

a $C_1$-$C_{30}$ arylene radical such as a —$C_6H_4$-(ortho, meta or para) phenylene radical optionally substituted with a $C_1$-$C_{12}$ alkyl radical optionally containing 1 to 25 heteroatoms chosen from O, N, S, F, Si and P;

a $C_1$-$C_{30}$, such as $C_2$-$C_{12}$, alkarylene or aralkylene radical, and for example, a benzylene radical —$C_6H_4$—$CH_2$— optionally substituted with a $C_1$-$C_{12}$ alkyl radical optionally containing 1 to 8 heteroatoms chosen from O, N, S, F, Si and P;

an oxyalkylene or aminoalkylene radical, such as an alkylene oxide radical of formula —(R"O)$_y$R$^{iv}$ wherein R" is chosen from linear and branched $C_2$-$C_4$ alkyl radicals, R$^{iv}$ is chosen from hydrogen and linear and branched $C_1$-$C_{30}$ alkyl radicals, and y is a number ranging from 1 to 500 inclusive, such as from 1 to 250;

a mixture of these radicals.

In at least one embodiment, $R^{b2}$ is chosen from:

alkylene radicals having 1 to 12 carbon atoms or cycloalkylene radicals having 3 to 6 carbon atoms, optionally substituted with a $C_1$-$C_{12}$ alkyl radical such as methylene, ethylene, propylene, n-butylene, isobutylene, tert-butylene, n-pentylene, n-hexylene, n-octylene, n-dodecylene, n-octadecylene, cyclohexylene, cyclohexylmethylene, isophorone;

$C_1$-$C_{30}$, such as $C_2$-$C_{12}$, alkarylene or aralkylene radicals, optionally substituted with a $C_1$-$C_{12}$ alkyl radical such as a benzylene radical —$C_6H_4$—$CH_2$— or benzylene dimethylene.

Monomer (b2), in at least one embodiment, has a weight-average molecular weight (Mw) ranging from 60 to 1,000, for example, from 70 to 700 or from 80 to 500.

In at least one embodiment, monomers (b2) are chosen from:

aminoethanol; aminopropanol; 4-aminobutanol; 1-ethylaminobutan-2-ol; amino-2-methyl-2-propanol; methyl-4-amino-4-pentan-2-ol;

1,2-ethylenediamine; 1,2-propylenediamine; 1,3-propylenediamine; 1,4-diaminobutane; 1,5-diaminopentane; 1,6-diaminohexane; 2,6-toluenediamine;

1,4-butanediol; 1,6-hexanediol; 1,2-ethanediol; 1,2-propanediol; 1,3-propanediol;

neopentylglycol; di(ethyleneglycol) of formula HO—(CH$_2$CH$_2$O)$_2$H; dihydroxylated poly(ethylene oxide)s; dihydroxylated poly(propylene oxide)s; dihydroxylated poly(ethylene oxide/propylene oxide) copolymers; 1,2-benzenedimethanol; 1,4-benzenedimethanol; 1,4-dimethylol-cyclohexane;

1,2-benzenethiol; and mixtures thereof.

When monomer (b2) comprises at least one junction group (A), it can be chosen from the compounds of formula:

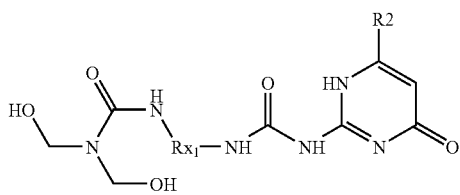

wherein R2 and Rx$_1$, are as defined above.

Ionizable Group

In at least one embodiment of the disclosure, the copolymer can comprise at least one ionizable group, which can be present on at least one part of the monomers of type (b2) and/or on at least one part of the junction groups (A), for example, on at least one part of the monomers (b2).

"Ionizable group" means, according to the disclosure, any group which, by its intrinsic chemical nature, or as a function of the medium and/or of the pH of the medium in which it occurs, can be of ionic form. Depending on its chemical nature, it can be cationizable, anionizable or amphoteric. This therefore includes the ionic groups such as the tetra-N-substituted quaternary ammonium groups.

The (thio)urethane/(thio)urea copolymers according to the disclosure can therefore have at least one ionizable group, chosen from cationic, anionic and amphoteric groups and mixtures thereof, which promote their dispersion or dissolution in aqueous media.

In at least one embodiment, the ionizable groups are chosen from:

i) ionizable groups which form anions and their salts, such as the groups bearing an acid function chosen from:
the carboxyl radical: —COOH,
the sulphonic radical: —SO$_3$H,
the radical: OSO$_3$H,
the phosphonic radical: —(O)P(OH)$_2$,
the phosphoric radical: —OP(O)(OH)$_2$,
and their organic and inorganic salified forms.

The acid groups can be neutralized with a mineral base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for example, triethylamine or butylamine. This primary, secondary or tertiary alkylamine can contain at least one nitrogen and/or oxygen atom and can therefore have for example at least one alcohol functions; for example, amino-2-methyl-2-propanol, triethanolamine and dimethylamino-2-propanol. In at least one embodiment, the organic base may be chosen from lysine and 3-(dimethylamino)propylamine.

ii) ionizable groups that form cations and their salts, such as the groups containing a function chosen from:

a) amine radicals of formula —N(R$^v$)(R$^{vi}$) and their organic and inorganic salts, wherein R$^v$ and R$^{vi}$ are chosen from, independently of one another:

(i) hydrogen atoms,
(ii) linear, branched and cyclic, saturated and unsaturated, optionally aromatic, alkyl groups having from 1 to 30 carbon atoms and optionally containing 1 to 10 heteroatoms chosen from O, N, S, and P, for example, methyl, ethyl, propyl, isopropyl, n-butyl, t-butyl, isobutyl, lauryl, or stearyl group;
(iii) alkylene oxide groups of formula —(R$^{vii}$O)rR$^{viii}$ wherein R$^{vii}$ is chosen from linear and branched C$_2$-C$_4$ alkyls, R$^{viii}$ is chosen from hydrogen and linear and branched C$_1$-C$_{30}$ alkyl radicals, and r is a number ranging from 1 to 250 inclusive;
(iv) R$^v$ and R$^{vi}$ can form, with the nitrogen atom, a saturated or unsaturated, optionally aromatic ring, comprising a total of 5, 6, 7 or 8 atoms, for example, 4, 5 or 6 carbon atoms and/or 2 to 4 heteroatoms chosen from O, S and N; and the ring can in addition be fused with at least one other saturated or unsaturated, optionally aromatic ring, each comprising 5, 6 or 7 atoms, for example, 4, 5, 6 or 7 carbon atoms and/or 2 to 4 heteroatoms chosen from O, S and N;

b) groups of the structure —R$^{ix}$—N—R$^x$— wherein R$^{ix}$ and R$^x$ form, with the nitrogen atom, a saturated or unsaturated, optionally aromatic ring comprising a total of 5, 6, 7 or 8 atoms, for example, 4, 5 or 6 carbon atoms and/or 2 to 4 heteroatoms chosen from O, S and N; and the ring can be fused with at least one other saturated or unsaturated, optionally aromatic ring, each comprising 5, 6 or 7 atoms, for example, 4, 5, 6, 7 or 8 carbon atoms and/or 2 to 4 heteroatoms chosen from O, S and N, for example, the ionizable group can constitute an aromatic or non-aromatic ring having a cationizable tertiary amine group or can be an aromatic or non-aromatic heterocycle, containing a cationizable tertiary nitrogen;

c) guanidino or amidino groups of the respective formulae:

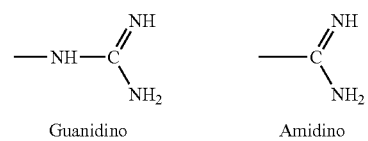

Guanidino    Amidino d) the quaternary ammonium groups of formula:

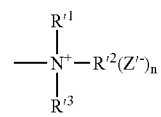

wherein:
the groups R$'^1$, R$'^2$ and R$'^3$ are chosen from, independently of one another, linear and branched C$_1$-C$_{20}$ alkyl groups,
n is a number in the range from 0 to 1,
and Z$'^-$ is chosen from a halide ion such as Br$^-$ or Cl$^-$ (n=1), or an ion CH$_3$SO$_3^-$ or a sulphate ion SO$_4^{2-}$ (n=½) or mixtures thereof;

e) and mixtures thereof.

In at least one embodiment, the ionizable groups are chosen from the pyridinyl, indolyl, isoindolinyl, imidazolyl, imidazolinyl, piperidinyl, pyrazolyl, quinoline, pyrazolinyl, piperazinyl, pyrrolidinyl, quinidinyl, thiazolinyl, morpholine, guanidino, and amidino radicals, and combinations thereof.

The amine units can optionally be neutralized. In at least one embodiment, the salts are chosen from mineral acids, such as sulphuric acid, hydrochloric acid, and phosphoric acid. Non-limiting mention may also be made of the salts of organic acids, which can have at least one carboxylic, sulphonic, or phosphonic acid group. They may be linear, branched or cyclic aliphatic acids, or aromatic acids. These acids can have, in addition, at least one heteroatom chosen from O and N, for example in the form of hydroxyl groups. Non-limiting acid examples include propionic acid, acetic acid, terephthalic acid, citric acid, tartaric acid and lactic acid.

It should be noted that the neutralization of the acid or amine units, as well as quaternization, can be complete or partial; it can for example, range from 5 to 100%, or from 20 to 95%.

In at least one embodiment, these ionizable groups can be chosen from:

the following ionizable groups which form anions: the monovalent groups —COOH, —CH$_2$COOH, —(CH$_2$)$_2$COOH, —(CH$_2$)$_3$COOH, —(CH$_2$)SO$_3$H, —(CH$_2$)$_2$SO$_3$H, —(CH$_2$)$_3$SO$_3$H, —O(CH$_2$)$_3$SO$_3$H; the divalent groups —C(COOH)(CH$_3$)— and —CH$_2$—C(COOH)(CH$_3$)—CH$_2$—; for which the neutralizing agents can be chosen from NaOH, KOH, Ca(OH)$_2$, NH$_4$OH, triethylamine, butylamine, amino-2-methyl-2-propanol, triethanolamine, dimethylamino-2-propanol, lysine and 3-(dimethylamino)propylamine; and the following tionizable groups that form cations: the monovalent groups —(CH$_2$)$_2$—N(CH$_3$)$_2$, —N(CH$_3$)$_2$, —(CH$_2$)$_3$—N(CH$_3$)$_2$, —O—(CH$_2$)$_3$—N(CH$_2$CH$_3$)$_2$, —(CH$_2$)$_2$—N(CH$_2$CH$_3$)$_2$; the divalent groups —(CH$_2$)$_2$—N(CH$_3$)—(CH$_2$)$_2$— and —(CH$_2$)$_3$—N(CH$_3$)—(CH$_2$)$_3$—; for which the neutralizing agents can be chosen from HCl, propionic acid, acetic acid, citric acid and tartaric acid.

As mentioned above, at least one of the junction groups (A) can bear at least one ionizable group as defined above.

In at least one embodiment, at least one of the radicals R1, R2 and/or R3 of the junction groups (A) can bear an ionizable group as defined above.

The ionizable group can also be carried by the monomer (b1); in this case, the monomer (b1) can be chosen from the sulphonic polyesters and the ethylenic copolymers based on maleic anhydride.

In at least one embodiment, the ionizable group can be carried by all or part of the monomers (b2) as defined above.

In at least one embodiment, ionizable monomers (b2) which form anions are chosen from monomers bearing carboxylic (—COOH) and sulphonic (—SO$_3$H) functions, for example those of formula:

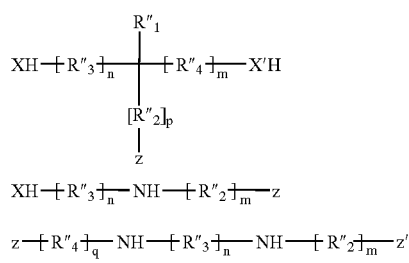

-continued

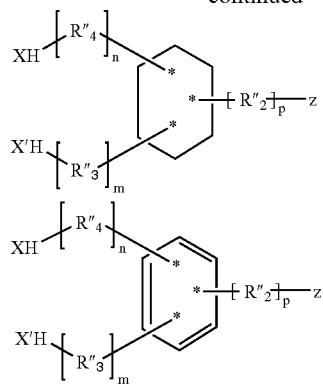

wherein:

R"$_1$ is chosen from hydrogen atoms and alkyl groups having from 1 to 40 carbon atoms, linear and branched, cyclic and non-cyclic, saturated and unsaturated, aromatic and non-aromatic, and/or optionally comprising at least one heteroatom chosen from O, S, P and N, and/or optionally substituted with at least one fluorine or silicon atom; the heteroatom or heteroatoms, when present, can be inserted in the chain of the group, or alternatively the group can be substituted with at least one group containing them, such as hydroxyl or amino groups (NH$_2$, NHR' or NR'R" wherein R' and R", which may be identical or different, are chosen from linear and branched C$_1$-C$_{22}$ alkyl groups, such as methyl or ethyl);

R"$_2$, R"$_3$ and R"$_4$, which may be identical or different, are chosen from alkylene groups (divalent alkyls) having from 1 to 40 carbon atoms, linear and branched, cyclic and non-cyclic, saturated and unsaturated, aromatic and non-aromatic, and/or optionally comprising at least one heteroatom chosen from O, S, P and N, and/or optionally substituted with at least one fluorine or silicon atom; the heteroatom or heteroatoms, when present, can be inserted in the chain of the group, or alternatively the group can be substituted with at least one group containing them, such as the ester, amide, hydroxyl or amino groups (NH$_2$, NHR' or NR'R" wherein R' and R", which may be identical or different, are chosen from linear and branched C$_1$-C$_{22}$ alkyl groups, such as methyl or ethyl);

X and X', which may be identical or different, are chosen from O, S, NH, NR wherein R is chosen from linear and branched C$_1$-C$_6$ alkyl radicals; in at least one embodiment, X and X' are O;

Z, Z', which may be identical or different, are chosen from carboxylic acid functions (—COOH) and sulphonic acid functions (—SO$_3$H);

n, p, m and q are, independently of one another, equal to 0 or 1.

In at least one embodiment, the ionizable monomers (b2) which form anions are chosen from compounds of formula:

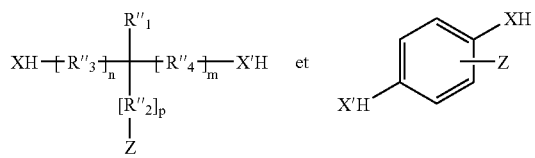

and
wherein X, X', R"$_1$, R"$_2$, R"$_3$, R"$_4$, m, n, p and Z are as defined above, and include the compounds of formula:

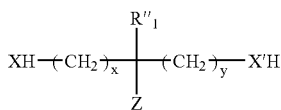

wherein R"$_1$ is chosen from alkyl groups having from 1 to 22 carbon atoms, such as CH$_3$, and x and y, which may be identical or different, are integers ranging from 1 to 5 inclusive.

In at least one embodiment, ionizable monomers (b2) which form anions are chosen from dimethylolpropionic acid, dimethylaminopropionic acid, N-ethylsulphonic-dimethanolamine, N-ethylsulphonic-diethanolamine, and diolbenzene sulphonic acid.

These anionic groups can be neutralized as indicated above.

In at least one embodiment, the monomers (b2) may be chosen from the monomers bearing tertiary amine functions of formulae:

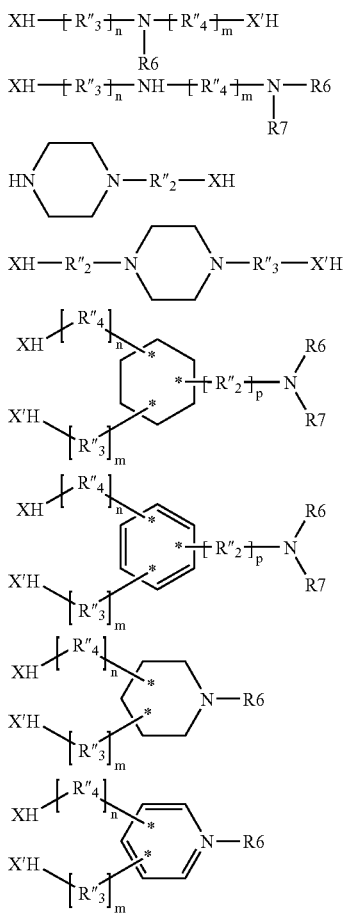

wherein:
R"$_2$, R"$_3$ and R"$_4$, which may be identical or different, are chosen from alkylene groups (divalent alkyl) having from 1 to 40 carbon atoms, linear and branched, cyclic and non-cyclic, saturated and unsaturated, aromatic and non-aromatic, and/or optionally comprising at least one heteroatom chosen from O, S, P and N, and/or optionally substituted with at least one fluorine or silicon atom; the heteroatom or heteroatoms, when present, can be inserted in the chain of the group, or alternatively the group can be substituted with at least one group containing them, such as the ester, amide, hydroxyl or amino groups (NH$_2$, NHR' or NR'R" wherein R' and R", which may be identical or different, are chosen from linear and branched C$_1$-C$_{22}$ alkyl groups, such as methyl or ethyl);

X and X', which may be identical or different, can be chosen from O, S, NH, and NR wherein R is chosen from linear and branched C$_1$-C$_6$ alkyl radicals; in at least one embodiment, X and X' are O;

n, p and m are, independently of one another, equal to 0 or 1;

R$_6$ and R$_7$ are chosen from linear and branched C$_1$-C$_{22}$ alkyl groups, such as methyl, ethyl, lauryl, and behenyl.

In at least one embodiment, the monomers (b2) are chosen from structures of formula:

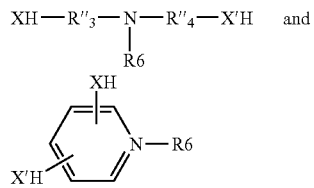

wherein X, X', R"$_3$, R"$_4$ and R6 are defined above.

According to at least one further embodiment, the monomers (b2) are chosen from N-methyldiethanolamine, N-tert-butyldiethanolamine, N-ethyldiethanolamine and diaminopyridine.

These cationic groups can be neutralized as indicated above.

In at least one embodiment, cationic or amphoteric monomers (b2) are chosen from those wherein the amine function is in a quaternary form, of formula:

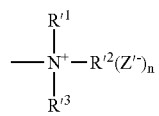

as defined above.

Quaternization of the tertiary amine groups can be carried out with compounds with a mobile halogen, for example, alkyl halides such as C$_1$-C$_{12}$ alkyl chlorides or bromides, and for example methyl bromide or ethyl chloride.

These groups can moreover be quaternized by compounds with a mobile halogen bearing carboxylic or sulphonic acid functions, such as sodium chloroacetate; or by cyclic sulphones, for example propanesulphone. In this way amphoteric monomers can be obtained (such as betaines, having at least one (+) charge and at least one (−) charge carried by the same monomer).

Quaternization can be effected on the polymer already synthesized or on the starting monomers, before polymerization.

The ionizable group, when present, can be present in an amount ranging from 0.1 to 50 wt. % relative to the total weight of the copolymer according to the disclosure, for example 0.5 to 35 wt. %, or 1 to 15 wt. %, relative to the total weight of the copolymer. Thus, the monomer or monomers bearing the ionizable group or groups can be present in an amount ranging from 3 to 20 wt. %, for example, 6 to 17 wt. % or 8 to 15 wt. %, of the total weight of the final copolymer.

The copolymer according to the disclosure can also comprise, optionally, monomers of structure YCN—$R_{10}$, wherein Y is chosen from O and S; for example, O; and $R_{10}$ is chosen from carbon-containing radicals, such as alkyl groups, having from 1 to 40 carbon atoms, linear and branched, cyclic and non-cyclic, saturated and unsaturated, aromatic and non-aromatic, optionally comprising at least one heteroatom chosen from O, S, P and N, and/or optionally substituted with at least one fluorine or silicon atom; the heteroatom or heteroatoms, when present, can be inserted in the chain of the radical, or alternatively the radical can be substituted with at least one group containing them such as the ester and/or amide groups.

In at least one embodiment, $R_{10}$ can bear at least one junction group (A).

For example, YCN—$R_{10}$ can correspond to the formula:

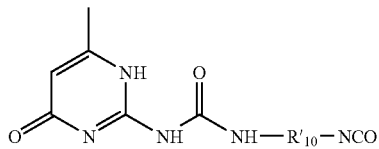

wherein $R'_{10}$ is a divalent carbon-containing radical chosen from linear and branched $C_1$-$C_{30}$ alkyl groups, $C_4$-$C_{12}$ cycloalkyl groups and $C_4$-$C_{12}$ aryl groups; comprising optionally 1 to 8 heteroatoms chosen from O, N, S, F, Si and P; as well as from mixtures of these groups.

The copolymer according to the disclosure can also comprise, optionally, monomers of structure HX—$R_{11}$ wherein:
X is chosen from O, S, NH and NR, wherein R is chosen from $C_1$-$C_6$ alkyl groups; in at least one embodiment, X=O; and
$R_{11}$ is chosen from carbon-containing radicals, such as alkyl groups, having from 1 to 40 carbon atoms, linear and branched, cyclic and non-cyclic, saturated and unsaturated, aromatic and non-aromatic, optionally comprising at least one heteroatom chosen from O, S, P and N, and/or optionally substituted with at least one fluorine or silicon atom; the heteroatom or heteroatoms, when present, can be inserted in the chain of the radical, or alternatively the radical can be substituted with at least one group containing them such as ester and/or amide groups.

Structure of the Copolymers According to the Present Disclosure

In at least one embodiment, the copolymers of the disclosure have a polymer skeleton having a degree of polymerization in ranging from 3 to 20,000, for example, from 5 to 10,000 or from 10 to 5,000.

The copolymers according to the disclosure can comprise polyurethane and/or polyurea and/or polythiourethane and/or polythiourea sequences for example corresponding to the following formula:

wherein:
X and X' are chosen from monomers (b), such as monomers (b1) and (b2), and are as defined above,
Y and Y' are chosen from monomers (a), whether of type (a1) and/or (a2), and are as defined above, radicals $R^b$ are chosen from monomers (b), namely (b1) and (b2), for example, they are, randomly, $R^{b1}$ and $R^{b2}$ as defined above;
radicals $R^a$ are chosen from from monomers (a), and are as defined above; for example, they are, randomly, the monomers $R^a$ of divalent aliphatic radical type (a1) and the monomers $R^a$ of polymeric type (a2);
provided at least one of the radicals $R^a$ and/or $R^b$ comprises at least one junction group A capable of forming at least 3 hydrogen bonds; and
x is an integer ≥2.

The number-average molecular weight Mn of the copolymer according to the disclosure, in at least one embodiment, ranges from 1,000 and 3,000,000, for example from 5,000 to 1,000,000, or from 8,000 to 500,000.

In at least one embodiment, the molar ratio between all of the monomers of formula YCN—$R^a$—NCY' and all of the monomers of formula HX—$R^b$—X'H (namely the monomers (b1) and (b2)) ranges from 0.5 to 2, for example, from 0.6 to 1.5 or from 0.7 to 1.3; in at least one further embodiment, this ratio is 1.

According to at least one embodiment, the monomers of type HX—$R^{b1}$—X'H (polymer) are present in an amount ranging from 10 to 95 wt. %, for example from 12 to 85 wt. %, or from 15 to 80 wt. %, of the total weight of the final polymer.

In at least one embodiment, the monomers of type HX—$R^{b2}$—X'H (small diol) are present in an amount ranging from 1 to 30 wt. %, for example from 2 to 25 wt. %, or from 3 to 20 wt. %, of the total weight of the final polymer.

According to at least one embodiment, the copolymer according to the disclosure has 1 to 12 junction groups (A), for example ranging from 2 to 10, or from 3 to 8, or from 4 to 6, junction groups (A), per polymer chain.

The copolymers according to the disclosure can have two glass transition temperatures, in at least embodiment, a first glass transition temperature, Tg1, is less than or equal to 0° C., and a second glass transition temperature, Tg2, is greater than or equal to 20° C.

According to at least one embodiment, the copolymers of the disclosure have units that are chosen from polymeric monomers (b1) bearing reactive functions with a labile hydrogen (XH) at their ends, and which can have a glass transition temperature (Tg) below 20° C., for example, below 10° C., and such as below 0° C.

Synthesis of the Copolymers According to the Disclosure:

The copolymers according to the disclosure, for example the (thio)urethane/(thio)urea copolymers, can be prepared according to usual methods of polycondensation familiar to a person skilled in the art. These methods are for example described in the following works:
  60 Years of PUR—J. E. Kresta, E. W. Eldred Ed. Technomic Publishing, 1998;
  Waterborne and Solvent-Based Surface Coating Resins and Their Application, Surface Coating Technology Series, Vol. 3, Polyurethanes, Paul Thomas, John Wiley & Sons, 1998.

For purposes of illustration, a general synthetic scheme is given below, to which a person skilled in the art can refer:
  the monomer or monomers having a labile hydrogen (b1) and (b2) are reacted with the monomer or monomers (a) in an organic solvent, with or without a catalyst;
  the organic solvent used is may be chosen so that it is inert with respect to the isocyanate groups. It is for example chosen from the group comprising acetone, methyl ethyl ketone, ethyl acetate or butyl acetate, tetrahydrofuran, 1,2-dichloroethane and mixtures thereof;

the optional catalyst can be chosen from the derivatives of tin or of titanium, for example 2-ethyltin hexanoate and dibutyltin dilaurate;

polymerization can be carried out at a temperature ranging from 20 to 120° C., for example, from 50 to 100° C.;

the copolymer of the disclosure thus obtained can then be purified if required, for example by precipitation in a non-solvent.

When the copolymer is intended to be used in hydrophilic medium, for example, aqueous media, a stage of aqueous dissolution may be necessary; in this case, the polymer may have ionizable groups in the context of the present disclosure.

It may be possible to prepare an aqueous solution or dispersion of the copolymer according to the disclosure in the following way:

the copolymer can be dissolved by simple addition of water, in at least one embodiment, if it has a sufficient quantity of ionizable groups, for example at least ranging from 3 to 20 wt. % of monomers bearing such groups, such as from 6 to 17 wt. %, or from 8 to 15 wt. %, relative to the total weight of the copolymer.

the copolymer, in at least one embodiment, when it has ionizable groups, can be dissolved or dispersed in water by simple addition of neutralizing agent in aqueous solution. In this case, the polymer can be obtained in water-soluble or water-dispersible form.

the copolymer, in at least one embodiment, when it has ionizable groups, can also be dissolved or dispersed in water by a method of dissolution in a volatile organic solvent, then addition of water and of neutralizing agent, and finally evaporation of the organic solvent. In this case, the polymer may be obtained in the form of aqueous dispersion.

According to a variant of the method, neutralization of the ionizable functions of the copolymer can be carried out during actual formation of the polymer.

After obtaining the copolymer in the organic solvent, an aqueous emulsion can then be prepared by pouring, with stirring, into the organic solution obtained, a suitable amount of water containing a neutralizing agent and optionally an antifoaming agent, the role of which will be to facilitate subsequent evaporation of the organic phase.

During formation of the emulsion, stirring is for example carried out with a shearing disperser of the Moritz or Ultraturax or Raineri type equipped with deflocculating blades.

The emulsion thus obtained can be particularly stable without needing to use a surfactant since the ionic groups of the copolymers may be located at the interface with the water and protect the droplets from coalescence by electrostatic repulsion.

After formation of the emulsion at a temperature ranging from room temperature (20-25° C.) to 70° C., the organic solvent can be evaporated at reduced pressure until it has been removed completely, the evaporation may be carried out with gentle heating.

Finally an aqueous dispersion of particles of the copolymer, for example of polyurethane, is obtained which is free from any surfactant or any other hydrophilic stabilizer, yet can be very stable.

The average size of the particles as well as their polydispersity can be controlled by varying, during preparation of the dispersion, the respective proportions of copolymer, organic solvent and water, or by varying the degree of neutralization or the nature of the neutralizing agent.

According to at least one embodiment, the dispersion may have an average particle size ranging from 5 to 400 nanometers, for example from 10 to 250 nanometers, measured by quasi-elastic diffusion of light.

The polydispersity with respect to size of the particles, measured by quasi-elastic diffusion of light, can be less than 0.5, for example, less than 0.3.

It is to be understood that formation of a solution or of a dispersion depends on the nature of the copolymer and/or of the neutralizing agent used.

The copolymers, for example polyurethanes, according to the disclosure can be plasticized to improve film formation at room temperature. Plasticization can be performed using conventional non-polymeric plasticizers. In at least one embodiment the plasticizer can be a good solvent of the copolymer, for example polyurethane, according to the disclosure and may be insoluble in water. In at least one embodiment, the hydrophobic plasticizers are chosen from:

diethyl, dibutyl and 2-diethylhexyl phthalates and adipates, diethyl and dibutyl tartrates, diethyl, dibutyl and 2-diethylhexyl phosphates, propylene glycol derivatives chosen from propylene glycol phenyl ether, propylene glycol diacetate, dipropylene glycol butyl ether, and tripropylene glycol butyl ether, glycerol esters such as glycerol triacetate (triacetin), and propylene glycol monophenyl ether sold under the name "Dowanol PPH" by Dow Chemical and dipropylene glycol n-butyl ether sold under the name "Dowanol DPnB" by Dow Chemical.

The plasticizer can be incorporated either after making the dispersion, or during preparation of the dispersion: in that case the plasticizer is incorporated in the organic phase.

The copolymers, such as polyurethanes, according to the disclosure therefore can make it possible to prepare aqueous dispersions or solutions that are very fluid and, moreover, stable without using additional surfactants, provided they also have ionic functions.

The copolymers of the present disclosure can also be dissolved or dispersed in esters, alcohols, carbon-containing and/or silicone-containing oils and mixtures thereof.

The disclosure also relates to the use of at least one copolymer according to the disclosure in cosmetic compositions to improve the viscoelastic properties of cosmetic deposits and films obtained from these compositions.

The cosmetic compositions according to the disclosure, in at least one embodiment, contain the copolymers according to the disclosure, alone or mixed, in an amount ranging from 0.01 to 90 wt. %, for example from 0.1 to 85 wt. %, or from 0.5 to 80 wt. %, relative to the total weight of the composition.

The compositions according to the disclosure can be in all the galenical forms conventionally used for topical application and in the form of an aqueous, alcoholic or aqueous-alcoholic solution or suspension, or an oily solution or suspension, or a solution or dispersion of the lotion or serum type, an emulsion of a liquid or semi-liquid consistency of the milk type, obtained by dispersing an oil phase in an aqueous phase (O/W) or vice versa (W/O), or a suspension or emulsion of a soft consistency of the cream type (O/W) or (W/O), or an aqueous or anhydrous gel, an ointment, a loose or compacted powder to be used as such or to be incorporated in an excipient, or of any other cosmetic form.

The cosmetic or pharmaceutical compositions according to the disclosure comprise, in addition to the copolymers, a medium that is physiologically acceptable, for example, cosmetically or pharmaceutically acceptable, such as dermatologically acceptable, for example, a medium that is compatible with the cutaneous tissues such as the skin of the face or of the body, and keratinous materials such as the hair, eyelashes, eyebrows and nails.

The physiologically acceptable medium may be a medium that does not adversely affect the properties of increased persistence of at least one cosmetic and/or care effect, of adhesion to keratinous materials and ease of make-up removal provided by the composition after application.

In at least one embodiment, the physiologically acceptable medium comprises a medium that is a solvent of the copolymers according to the disclosure, which can contain at least one compound chosen from water, alcohols, polyols, esters, carbon-containing oils, silicone oils, fluorinated silicone oils, and mixtures thereof. The oils can be polar or apolar.

Thus, the solvent medium of the compositions according to the disclosure can comprise water or a mixture of water and at least one hydrophilic organic solvent such as alcohols for example, linear and branched $C_1$-$C_6$ monohydric alcohols such as ethanol, tert-butanol, n-butanol, isopropanol or n-propanol, or 2-butoxy-ethanol; and polyols such as glycerol, diglycerol, ethylene glycol, propylene glycol, sorbitol, pentylene glycol, and polyethylene glycols, or alternatively glycol ethers, for example $C_2$ such as monoethyl ether and monomethyl ether of diethylene glycol, and hydrophilic $C_2$-$C_4$ aldehydes.

The solvent medium can comprise alcohols incorporating an aromatic group such as benzyl alcohol or phenoxyethanol, their derivatives, carboxylic esters, and mixtures thereof.

In at least one embodiment, the carboxylic esters may be chosen from those having 2 to 8 carbon atoms, for example, ethyl acetate and butyl acetate, methyl acetate, propyl acetate, n-butyl acetate, and isopentyl acetate.

The solvent medium can also comprise physiologically acceptable organic solvents, chosen from ketones that are liquid at room temperature such as methyl ethyl ketone, methyl isobutyl ketone, diisobutyl ketone, isophorone, cyclohexanone, acetone; propylene glycol ethers that are liquid at room temperature such as propylene glycol monomethyl ether, propylene glycol monomethyl ether acetate, dipropylene glycol mono n-butyl ether; ethers that are liquid at 25° C. such as diethyl ether, dimethyl ether or dichlorodiethyl ether; alkanes that are liquid at 25° C. such as decane, heptane, dodecane, isododecane, cyclohexane; aromatic cyclic compounds that are liquid at 25° C. such as toluene and xylene; aldehydes that are liquid at 25° C. such as benzaldehyde, acetaldehyde and mixtures thereof.

The solvent medium can also comprise cosmetic oils, polar or apolar, carbon-containing or silicone oils, of animal, vegetable, mineral or synthetic origin.

In at least one embodiment the polar oils are chosen from carbon-containing oils which can contain ester, ether, acid and/or alcohol functions, such as:
carbon-containing vegetable oils with high content of triglycerides comprising esters of fatty acids and of glycerol, wherein the fatty acids can have various lengths of chains, which can be linear and branched, saturated and unsaturated; these oils include wheat germ oil, maize oil, sunflower oil, shea butter, castor oil, sweet almond oil, macadamia oil, apricot oil, soya oil, colza oil, cottonseed oil, alfalfa oil, poppyseed oil, Chinese okra oil, sesame oil, squash oil, avocado oil, hazelnut oil, grape seed or black currant seed oil, evening primrose oil, millet oil, barley oil, quinoa oil, olive oil, rye oil, safflower oil, candlenut oil, passionflower oil, musk rose oil; or the triglycerides of caprylic/capric acids such as those sold by the company Stéarineries Dubois or those sold under the names Miglyol 810, 812 and 818 by the company Dynamit Nobel;

the synthetic oils of formula $R^{11}COOR^{12}$ wherein $R^{11}$ is chosen from residues of fatty acids, linear and branched, having from 7 to 19 carbon atoms, and $R^{12}$ is chosen from branched hydrocarbon chains containing from 3 to 20 carbon atoms, for example Purcelline oil (cetearyl octanoate), isononyl isononanoate, $C_{12}$-$C_{15}$ alkyl benzoates;

synthetic esters and ethers such as isopropyl myristate, ethyl-2-hexyl palmitate, octanoates, decanoates or ricinoleates of alcohols or of polyalcohols;

hydroxylated esters such as isostearyl lactate, diisostearyl malate, and esters of pentaerythritol;

$C_8$-$C_{26}$ aliphatic alcohols such as oleic alcohol; and mixtures thereof.

In at least one embodiment, apolar oils may be chosen from:
silicone oils, volatile and non-volatile, linear and cyclic, liquid at room temperature, such as the polydimethylsiloxanes (PDMS) bearing alkyl, alkoxy or phenyl groups, pendent and/or at the end of the silicone chain, and having from 2 to 24 carbon atoms; phenylated silicones, such as the phenyl trimethicones, phenyl dimethicones, phenyl trimethylsiloxydiphenylsiloxanes, diphenyl dimethicones, diphenyl methyltrisiloxanes, 2-phenylethyl trimethylsiloxysilicates, and hydrocarbons and fluorinated hydrocarbons or fluorocarbons, linear and branched, of synthetic or mineral origin, such as volatile oils, such as the paraffin oils (for example isoparaffins and notably isododecane), or non-volatile and their derivatives, such as petroleum jelly, polydecenes, hydrogenated polyisobutene such as parleam, squalane, and mixtures thereof.

In at least one embodiment, the solvent medium can be present in an amount ranging from 1 to 90 wt. %, for example, from 5 to 70 wt. %, relative to the total weight of the composition.

The solubility of the copolymers according to the disclosure can be controlled by selection of the polymer skeletons -POL- and/or the junction groups (A).

The copolymers of the disclosure can in certain cases interact with one another physically (establishing an H bond network) in certain solvents or mixtures of solvents. This depends for example, on the nature and the proportions of solvents or mixtures of solvents used. This can give rise to an undesirable increase in viscosity of the composition and possibly interfere with its application (for example lotion, aerosol, etc.).

In at least one embodiment, to overcome this problem of viscosity, it is possible to:
dissolve the copolymer according to the disclosure in a volatile solvent capable of establishing H bonds with junction groups (A), for example using short, $C_1$-$C_4$ alcohols, volatile polyols, water and/or a mixture of these solvents, or use a two-phase solvent medium, for example a water-in-oil (W/O) or oil-in-water (O/W) emulsion and a pair of selective copolymers according to the disclosure whose junction groups and polymer skeletons are of different chemical nature, each polymer being dissolved in a different phase (one in the water, the other in the oil).

In embodiments having this problem of viscosity, the pair of copolymers $A_1$-$POL_1$-$A_1$ and $A_2$-$POL_2$-$A_2$ can be chosen in such a way that:

each of the junction groups ($A_1$) does not establish H bonds with itself but only with ($A_2$), each of the junction groups ($A_2$) does not establish H bonds with itself but only with ($A_1$), the junction groups ($A_1$) and ($A_2$) only establish H bonds when they are brought into contact, and the polymer skeletons -$POL_1$- and -$POL_2$- are chosen in such a way that the copolymers $A_1$-$POL_1$-$A_1$ and $A_2$-$POL_2$-$A_2$ can each be dissolved or dispersed in a phase separate from the emulsion, so that they are unable to react in the emulsion.

Interaction might only take place between the two copolymers on application, provided however that the solvent media are volatile solvents or can penetrate into the keratinous substrate.

The composition of the disclosure can also contain the additives that are usually employed in the cosmetic or pharmaceutical field, provided that the additive does not adversely affect the properties required for the composition of the disclosure, such as waxes, gums, surfactants, thickeners, hydrophilic or lipophilic gelling agents, hydrophilic or lipophilic cosmetic actives, preservatives, antioxidants, perfumes, luster agents, fillers, neutralizing agents, copolymers other than those defined previously, emulsifiers and co-emulsifiers, pigments, and dyes.

A person skilled in the art will of course take care to select any optional additives and/or their amount, in such a way that the advantageous properties of the composition according to the disclosure are not, or substantially not, adversely affected by the addition that is envisaged.

The amounts of these various additives are those conventionally used in the fields in question, for example ranging from 0.001 to 30% of the total weight of the composition. Depending on their nature, these additives can be introduced in the oil-phase, in the aqueous phase, in the lipid vesicles and/or in the nanoparticles.

"Wax", in the context of the present disclosure, means a lipophilic compound, solid at room temperature (25° C.), with reversible solid/liquid change of state, having a melting point greater than or equal to 25° C. and up to 120° C. By bringing the wax to the liquid state (fusion), it is may be possible to make it miscible with any oils that are present, and form a miscroscopically homogeneous mixture, but when the temperature of the mixture returns to room temperature there is recrystallization of the wax in the oils of the mixture. The melting point of the wax can be measured using a differential scanning calorimeter (DSC), for example the calorimeter sold under the name DSC 30 by the company METTLER.

The waxes optionally present in the disclosed compositions can be hydrocarbon waxes, fluorinated waxes and/or silicone waxes and can be of vegetable, mineral, animal and/or synthetic origin. In at least one embodiment, the waxes have a melting point above 30° C., such as above 45° C. The following waxes can be used in the composition of the disclosure: beeswax, Carnauba or Candellila wax, paraffin, microcrystalline waxes, ceresin or ozokerite, synthetic waxes such as polyethylene waxes or Fischer-Tropsch waxes, and silicone waxes such as alkyl or alkoxy-dimethicone having from 16 to 45 carbon atoms.

The gums can be high molecular weight polydimethylsiloxanes (PDMS) or cellulose gums or polysaccharides and the pastes can be hydrocarbon compounds such as lanolins and their derivatives or alternatively PDMS.

The nature and amount of the waxes and/or gums depend on the required mechanical properties and textures. As a guide, the composition can contain an amount ranging from 0.1 to 50 wt. % of waxes, relative to the total weight of the composition for example, from 1 to 30 wt. %.

The composition according to the disclosure can additionally contain, in a particular phase, pigments and/or nacres and/or fillers that are usually employed in cosmetic compositions.

The composition can also contain coloring matter other than pigments and nacres, chosen from water-soluble dyes and fat-soluble dyes that are familiar to a person skilled in the art. All of these colorants can be used in mixtures.

According to the present disclosure, "pigments" means particles of any shape, white or colored, mineral or organic, insoluble in the physiological medium, and intended to color the composition.

In the context of the present disclosure, "fillers" means colorless or white particles, mineral or synthetic, lamellar or non-lamellar, intended to give body or stiffness to the composition, and/or softness, matte appearance and uniformity to make-up.

According to the present disclosure, "nacres" means iridescent particles of any shape, for example, produced in the shell of certain molluscs, or synthesized.

Pigments can be present in the composition in an amount ranging from 0.01 to 25 wt. % of the final composition, for example, from 3 to 10 wt. %. They can be white or colored, inorganic or organic. Non-limiting examples include the titanium, zirconium or cerium oxides, as well as the zinc, iron or chromium oxides, ferric blue, chromium hydroxide, carbon black, ultramarines (polysulphides of aluminosilicates), manganese pyrophosphate and certain metal powders such as those of silver or of aluminium. Further non-limiting examples include the D&C pigments and the lakes commonly employed for imparting a make-up effect to the lips and to the skin, which include salts of calcium, of barium, of aluminium, of strontium or of zirconium.

Nacres can be present in the composition in an amount ranging from 0.01 to 20 wt. %, for example from 3 to 10 wt. %. Among the nacres that can be envisaged, non-limiting examples include natural mother of pearl, mica coated with titanium dioxide, iron oxide, natural pigment or bismuth oxychloride as well as colored titanium mica.

Among the fat-soluble or water-soluble dyes that can be present in the composition, alone or as a mixture, in an amount ranging from 0.001 to 15 wt. %, for example from 0.01 to 5 wt. % or from 0.1 to 2 wt. %, relative to the total weight of the composition. Non-limiting examples include the disodium salt of ponceau, the disodium salt of alizarin green, quinoline yellow, amaranth trisodium salt, tartrazine disodium salt, rhodamine monosodium salt, fuchsin disodium salt, xanthophyll, methylene blue, carmine, halo-acid, azo and anthraquinone dyes, copper or iron sulphate, Sudan brown, Sudan red and annatto, as well as beetroot juice and carotene.

The composition according to the disclosure can additionally comprise at least one filler, for example at a content in an amount ranging from 0.01 to 50 wt. %, relative to the total weight of the composition, for example in an amount ranging from 0.02 to 30 wt. %. The fillers can be mineral or organic of any shape: as platelets, spherical or oblong. Non-limiting examples include talc, mica, silica, kaolin, powders of polyamide (Nylon®), of poly-β-alanine and of polyethylene, powders of tetrafluoroethylene polymers (Teflon®), lauroyl lysine, starch, boron nitride, hollow polymer microspheres such as those of polyvinylidene/acrylonitrile chloride such as Expancel® (Nobel Industrie), of copolymers of acrylic acid (Polytrap® from Dow Corning) and microbeads of silicone resin (Tospearls® from Toshiba, for example), particles of elastomeric polyorganosiloxanes, precipitated calcium carbonate, magnesium carbonate and hydrocarbonate, hydroxyapatite, hollow silica microspheres (Silica Beads® from Maprecos), glass or ceramic microcapsules, metal soaps derived from organic carboxylic acids having from 8 to 22 carbon atoms, such as from 12 to 18 carbon atoms, and for example zinc, magnesium or lithium stearate, zinc laurate, magnesium myristate.

The composition can also contain an additional polymer such as a film-forming polymer. According to the present disclosure, "film-forming polymer" means a polymer that is able to form, on its own or in the presence of a filming aid, a continuous film that adheres to a substrate, for example to keratinous materials. In at least one embodiment, the film-forming polymers that can be used in the composition of the present disclosure include synthetic polymers of radical or polycondensate type, polymers of natural origin and mixtures thereof, for example acrylic polymers, polyurethanes, polyesters, polyamides, polyureas, cellulosic polymers such as nitrocellulose.

In at least one embodiment, the (co)polymers of the disclosure can be used mixed with at least one of the copolymers described in International Patent Application No. WO 02/098377.

Although at least one embodiment of the present disclosure does not contain a surfactant, the composition can also contain at least one surfactant present in an amount ranging from 0.01 to 50 wt. %, for example from 0.1 to 40% or from 0.5 to 30%, relative to the total weight of the composition.

Such surfactants can be chosen from the anionic, amphoteric, non-ionic, and cationic surfactants or mixtures thereof.

In at least one embodiment, the anionic surfactants that can be used include, alone or mixed, salts (for example salts of alkali metals, such as of sodium, ammonium salts, salts of amines, salts of amino-alcohols or magnesium salts) of the following compounds: alkyl sulphates, alkylether sulphates, alkylamidoether-sulphates, alkylarylpolyether-sulphates, monoglyceride sulphates, alkyl sulphonates, alkyl phosphates, alkylamide sulphonates, alkaryl sulphonates, α-olefin sulphonates, paraffin sulphonates; alkyl sulphosuccinates, alkylether sulphosuccinates, alkylamide-sulphosuccinates, alkyl sulphosuccinamates, alkyl sulphoacetates, alkylether phosphates, acyl sarcosinates, acyl isethionates and N-acyl taurates, the alkyl or acyl radical of all these various compounds for example having from 8 to 24 carbon atoms, and an aryl radical such as a phenyl or benzyl group.

According to at least one embodiment, the salts include those of fatty acids, such as the salts of oleic, ricinoleic, palmitic, stearic acids, acids of copra oil or of hydrogenated copra oil, acyl lactylates whose acyl radical has 8 to 20 carbon atoms, alkyl D-galactoside uronic acids and their salts as well as the polyoxyalkylenated alkyl($C_6$-$C_{24}$)ether carboxylic acids, the polyoxyalkylenated alkyl($C_6$-$C_{24}$)aryl ether carboxylic acids, the polyoxyalkylenated alkyl($C_6$-$C_{24}$)amido-ether carboxylic acids and their salts, for example those having from 2 to 50 ethylene oxide groups, and mixtures thereof.

In at least one embodiment, the non-ionic surfactants that can be used, include, alone or mixed, alcohols, alpha-diols, alkyl phenols or polyethoxylated, polypropoxylated or polyglycerolated fatty acids, having an aliphatic chain with for example 8 to 18 carbon atoms, where the number of ethylene oxide or propylene oxide groups can optionally be in the range from 2 to 50 and the number of glycerol groups can optionally be in the range from 2 to 30.

According to at least one embodiment, non-limiting examples of non-ionic surfactants include the copolymers of ethylene oxide and propylene oxide, the condensates of ethylene oxide and propylene oxide on aliphatic alcohols; polyethoxylated aliphatic amides, for example having from 2 to 30 moles of ethylene oxide, polyglycerolated aliphatic amides optionally having on average from 1 to 5 glycerol groups for example, from 1.5 to 4 glycerol groups; the oxyethylenated esters of fatty acids of sorbitan having from 2 to 30 moles of ethylene oxide; the esters of sucrose fatty acids, the esters of polyethylene glycol fatty acids, the alkyl polyglycosides, derivatives of N-alkyl glucamine, oxides of amines such as the alkyl($C_{10}$-$C_{14}$)amine oxides or the oxides of N-acylaminopropyl morpholine.

In at least one embodiment, the amphoteric surfactants that can be used include, alone or mixed, the derivatives of secondary or tertiary aliphatic amines wherein the aliphatic radical is a linear and branched chain with 8 to 22 carbon atoms and comprises at least one hydrosolubilizing anionic group (for example carboxylate, sulphonate, sulphate, phosphate or phosphonate); the alkyl ($C_8$-$C_{20}$) betaines, the sulphobetaines, the alkyl ($C_8$-$C_{20}$) amidoalkyl ($C_1$-$C_6$) betaines such as cocoamidopropyl betaine or the alkyl ($C_8$-$C_{20}$) amidoalkyl ($C_1$-$C_6$) sulphobetaines.

According to at least one embodiment, the cationic surfactants that can be used include, alone or mixed:

the quaternary ammonium salts of the following formula:

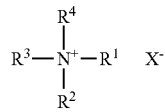

wherein X is an anion chosen from the halides (such as chloride, bromide or iodide) and alkyl($C_2$-$C_6$)sulphates such as methylsulphate, phosphates, alkyl or alkaryl sulphonates, anions derived from an organic acid such as acetate or lactate, and a) the radicals $R^1$ to $R^3$, which may be identical or different, are chosen from linear and branched aliphatic radicals having from 1 to 4 carbon atoms, and aromatic radicals such as aryl or alkaryl. The aliphatic radicals can bear heteroatoms such as oxygen, nitrogen, sulphur, and halogen atoms. The aliphatic radicals are for example chosen from the alkyl, alkoxy, and alkylamide radicals;

R4 is chosen from linear and branched alkyl radicals having from 16 to 30 carbon atoms.

In at least one embodiment, the cationic surfactant is a salt (for example chloride) of behenyl trimethyl ammonium.

b) the radicals $R^1$ and $R^2$, which may be identical or different, are chosen from linear and branched aliphatic radicals having from 1 to 4 carbon atoms, and aromatic radicals such as aryl or alkaryl. The aliphatic radicals can bear heteroatoms such as oxygen, nitrogen, sulphur, and halogen atoms. The aliphatic radicals are for example chosen from the alkyl, alkoxy, alkylamide and hydroxyalkyl radicals, having 1 to 4 carbon atoms;

$R^3$ and $R^4$, which may be identical or different, are chosen from linear and branched alkyl radicals having from 12 to 30 carbon atoms, the radical comprising at least one ester or amide function.

In at least one embodiment, $R^3$ and $R^4$ are chosen from the alkyl($C_{12}$-$C_{22}$)amido alkyl($C_2$-$C_6$), and alkyl($C_{12}$-$C_{22}$)acetate radicals.

According to at least one embodiment, the cationic surfactant is a salt (for example, chloride) of stearamidopropyl dimethyl (myristyl acetate) ammonium.

the quaternary ammonium salts of the imidazolinium type, for example those of the following formula:

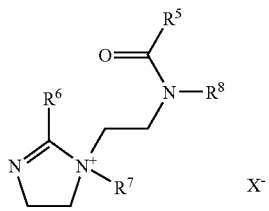

wherein $R^5$ is chosen from alkenyl or alkyl radicals having from 8 to 30 carbon atoms, for example derivatives of tallow fatty acids, $R^6$ is chosen from a hydrogen atom, $C_1$-$C_4$ alkyl radicals and alkenyl or alkyl radicals having from 8 to 30 carbon atoms, $R^7$ is chosen from $C_1$-$C_4$ alkyl radicals, $R^8$ is chosen from a hydrogen atom and $C_1$-$C_4$ alkyl radicals, X is an anion chosen from halides, phosphates, acetates, lactates, alkyl sulphates, alkyl and alkaryl sulphonates. In at least one embodiment, $R^5$ and $R^6$ are chosen from mixture of alkenyl or alkyl radicals having from 12 to 21 carbon atoms, for example derived from tallow fatty acids, $R^7$ is methyl, and $R^8$ is hydrogen. Such a product is for example Quaternium-27 (CTFA 1997) or Quaternium-83 (CTFA 1997) marketed under the names "REWOQUAT" W75, W90, W75PG, W75HPG by the company WITCO, the quaternary diammonium salts of the following formula:

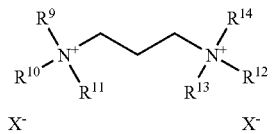

wherein $R^9$ is chosen from aliphatic radicals with from about 16 to 30 carbon atoms, $R^{10}$, $R^{11}$, $R^{12}$, $R^{13}$ and $R^{14}$, which may be identical or different, are chosen from hydrogen atoms and alkyl radicals having from 1 to 4 carbon atoms, and X is an anion chosen from halides, acetates, phosphates, nitrates and methylsulphates. Such quaternary diammonium salts, for example, comprise propane-tallow diammonium dichloride.

the quaternary ammonium salts comprising at least one ester function of the following formula:

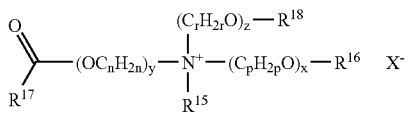

wherein:
$R^{15}$ is chosen from the $C_1$-$C_6$ alkyl radicals and the $C_1$-$C_6$ hydroxyalkyl or dihydroxyalkyl radicals;
$R^{16}$ is chosen from hydrogen, the radical $R^{19}$—C(O)— and the linear and branched, saturated and unsaturated $C_1$-$C_{22}$ hydrocarbon radicals $R_{20}$;
$R^{18}$ is chosen from hydrogen, the radical $R^{21}$—C(O)— and the linear and branched, saturated and unsaturated $C_1$-$C_{22}$ hydrocarbon radicals $R_{22}$;
$R^{17}$, $R^{19}$ and $R^{21}$, which may be identical or different, are chosen from the linear and branched, saturated and unsaturated $C_7$-$C_{22}$ hydrocarbon radicals;

n, p and r, which may be identical or different, are integers with a value from 2 to 6;
y is an integer with a value from 1 to 10;
x and z, which may be identical or different, are integers with a value from 0 to 10;
$X^-$ is chosen from simple and complex, organic and inorganic anions; provided that the sum x+y+z has a value from 1 to 15, and when x=0, $R^{16}$ denotes $R^{20}$, and when z=0, $R^{18}$ denotes $R^{22}$.

In at least one embodiment, the emulsifiers and co-emulsifiers that are optionally used in the composition, for example in the form of emulsion, include, depending on the type of emulsion (W/O or O/W), the fatty acid and polyol esters such as PEG-100 stearate, PEG-50 stearate and PEG-40 stearate; sorbitan tristearate, oxyethylenated sorbitan stearates comprising for example from 20 to 100 OE, and for example those available under the trade names Tween® 20 or Tween® 60, and their mixtures such as the mixture of glyceryl monostearate and polyethylene glycol stearate (100 OE) marketed under the designation SIMULSOL 165 by the company SEPPIC.

According to at least one embodiment, emulsifiers and co-emulsifiers that are optionally used in the composition include the siliconized emulsifiers such as the dimethicone copolyols and the alkyl dimethicone copolyols. An example of dimethicone copolyol includes the mixture of dimethicone copolyol, cyclomethicone and water (10/88/2) marketed by the company Dow Corning under the designation DC3225C or DC2-5225C, and an example of alkyl dimethicone copolyol includes, those having an alkyl radical with 10 to 22 carbon atoms, such as the cetyl dimethicone copolyol such as the product marketed under the designation Abil EM-90 by the company Goldschmidt and the mixture of dimethicone copolyol and cyclopentasiloxane (85/15) marketed under the designation Abil EM-97 by the company Goldschmidt; lauryl dimethicone copolyol and for example the mixture of 91% of lauryl dimethicone copolyol and 9% of isostearyl alcohol, marketed under the designation Q2-5200 by the company Dow Corning, and mixtures thereof.

In at least one embodiment, these emulsifiers and co-emulsifiers are present in the composition in a proportion in an amount ranging from 0.3 to 30 wt. %, for example from 0.5 to 20 wt. % relative to the total weight of the composition.

According to at least one embodiment, the hydrophilic gelling agents include the carboxyvinyl polymers (carbomers), the acrylic copolymers such as the acrylate/alkylacrylate copolymers, polyacrylamides, polysaccharides, natural gums and clays.

According to at least one embodiment, lipophilic gelling agents include modified clays such as the bentones, metal salts of fatty acids, and hydrophobic silica.

In at least one embodiment, the following may be used as cosmetic actives: depigmenting agents, emollients, moisturizers, trace elements, antiseborrheic agents, anti-acne agents, agents promoting hair regrowth, keratolytic and/or desquamating agents, antiwrinkle and stretching agents, anti-irritants, soothing agents, vitamins, UV filters, odor absorbers, antioxidants, agents against hair loss, anti-dandruff agents, propellants, ceramides, and mixtures thereof.

The compositions according to the disclosure can be in all the galenical forms conventionally used for topical application and for example, in the form of an aqueous, alcoholic or aqueous-alcoholic solution, dispersion or suspension or of an oily solution, optionally thickened or gelled; an oil-in-water, water-in-oil, or multiple emulsion, of liquid of semi-liquid consistency of the milk type or alternatively of soft consistency of the cream type; an aqueous or anhydrous gel; a mousse; an oily or emulsified gel; a dispersion of vesicles, for example of lipid vesicles; a two-phase or multiphase lotion; a spray; or any other cosmetic form.

A person skilled in the art will be able to select the appropriate galenical form, as well as its method of preparation, on the basis of his general knowledge, taking into account on the one hand the nature of the constituents used, for example their solubility in the vehicle, and on the other hand the application envisaged for the composition.

The cosmetic composition according to the disclosure can be in the form of a product for care, cleansing and/or make-up of the skin of the body or of the face, lips, eyelashes, nails and hair, a tanning or self-tanning product, a body hygiene product, a hairdressing product, for example for hair care, cleaning, styling or coloring.

In at least one embodiment, the composition can find application in the hairdressing field, for example for maintaining a hairstyle or for hair styling, or for cleaning the hair. The hairdressing compositions are for example shampoos, after-shampoos, hairdressing or hair care gels, care lotions or creams, conditioners, setting lotions, brushing lotions, fixing and styling compositions such as lacquers or sprays. The lotions can be packaged in various forms, for example in atomizers, pump-sprays or in aerosol containers to provide application of the composition in the form of spray or in the form of mousse.

According to at least one embodiment, the composition can be in the form of a hair coloring product, or in the form of a composition for perming, straightening, or bleaching, or in the form of compositions for rinsing, for application before or after coloring, bleaching, perming or straightening, or between the two stages of perming or straightening.

The composition according to the disclosure can also be in the form of a care composition, for example a moisturizer, for the skin, the lips and/or the integumentary appendages, or in the form of a skin cleansing composition, for example a make-up removal product or a bath or shower gel.

The composition can also be in the form of a care product, uncolored, intended for treating the skin such as for moisturizing, smoothing, depigmenting, nourishing, protecting from the sun's rays, or for providing a specific treatment. For this purpose, it may contain at least one care active chosen from depigmenting agents, emollients, moisturizers, antiseborrheic agents, anti-acne agents, agents promoting hair regrowth, keratolytic and/or desquamating agents, anti-wrinkle and stretching agents, anti-irritants, soothing agents, vitamins, filters, odor absorbers and mixtures thereof.

The composition can also be in the form of a body hygiene composition, such as in the form of a deodorant, antiperspirant, or in the form of a depilatory composition.

The composition can also be in the form of a product for make-up, for example colored, of the skin of the body or of the face, or of the hair, such as a foundation, optionally having care properties, a blush, a blusher or eye-shadow, a concealer, an eye-liner; a product for make-up of the lips such as a lipstick, optionally having care properties, a lip gloss, and lip pencils; a product for make-up of the integumentary appendages such as the nails, the eyelashes and for example in the form of a cake mascara, the eyebrows and the hair; a product for temporary tattooing of the skin of the body.

The disclosure also relates to a method of cosmetic treatment, for example make-up, care, cleansing and coloring, of keratinous materials, for example of the skin of the body or of the face, the nails, the hair, body hair and/or eyelashes, comprising the application of a cosmetic composition as defined previously on the materials.

Application can optionally be followed by rinsing with water. Thus, this method according to the disclosure provides maintenance of a hairstyle, cosmetic treatment, care, make-up, washing or make-up removal, among others, of the skin, of the hair and/or of any other keratinous material.

The disclosure also relates to a method for improving both the persistence of at least one effect supplied after deposition by a cosmetic composition and adhesion of the composition applied on keratinous materials, and also for permitting quick, complete and selective removal of the deposit, which comprises adding an effective amount of at least one copolymer according to the disclosure as defined previously, to the composition.

Removal of the deposit (or film) can comprise for example, rinsing of a cleansing composition or removal of a make-up deposit (such as lipstick, foundation, mascara, eye-liner). Removal can be carried out selectively using a solvent containing an agent for disrupting the hydrogen bonds, which is able to penetrate into the deposit.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The disclosure is illustrated in more detail in the following examples, wherein the amounts are given in percentage by weight. The equivalents (equiv) are molar equivalents.

Determination of Weight-Average Molecular Weight and Number-Average Molecular Weight The weight-average molecular weight (Mw) and number-average molecular weight (Mn) were determined by gel permeation liquid chromatography or GPC (solvent THF, calibration curve established with linear polystyrene reference standards, refractometric detector).

GPC was carried out with STYRAGEL HR4/7.8×300 mm columns, sold by Waters WAT044225.

Detection utilized a WATERS 410 refractometer.

The eluent was tetrahydrofuran (THF), at a flow rate of 1 ml/min.

The injected volume was 50 microlitres, at 25° C.

Determination of the Glass Transition Temperature (Tg)

The glass transition temperature was measured by differential scanning calorimetry (DSC) in the following conditions:

A film was made with a thickness of about 150 mm from the test polymer by depositing an aqueous solution or dispersion of the polymer in a circular Teflon die with a diameter of 40 mm and leaving the deposit to dry. The film was dried in a stove at a temperature of about 23° C. and relative humidity of 45%, until there was no longer any weight change. A sample was taken of about 5-15 mg of the film and put it in a crucible, which was then placed in the analyzer. The thermal analyser was a model DSC-2920 from TA INSTRUMENTS. The initial and final temperatures of temperature scanning were chosen so as to include the expected glass transition temperature. Temperature scanning was carried out at a rate of 10° C./min.

This analysis was carried out in accordance with standard ASTM D 3418-97 apart from the modifications stated above.

EXAMPLE 1

Preparation of a Diisocyanate-functionalized Ureidopyrimidone Monomer, of Formula

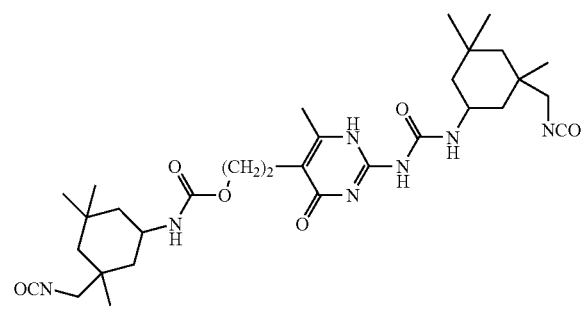

12 g of 5-(2-hydroxyethyl)-6-methyl-isocytosine was suspended in 150 ml of isophorone diisocyanate; the mixture was stirred under argon for 12 hours at 90° C. The resultant clear solution was cooled and precipitated in hexane. The precipitate was isolated by filtration, washed with hexane and then dried. 46 g of a solid was obtained, representing a yield of 93%.

EXAMPLE 2

Preparation of a Polyurethane-polyurea-polyester Copolymer Bearing an Ionizable Function Reactants Used:

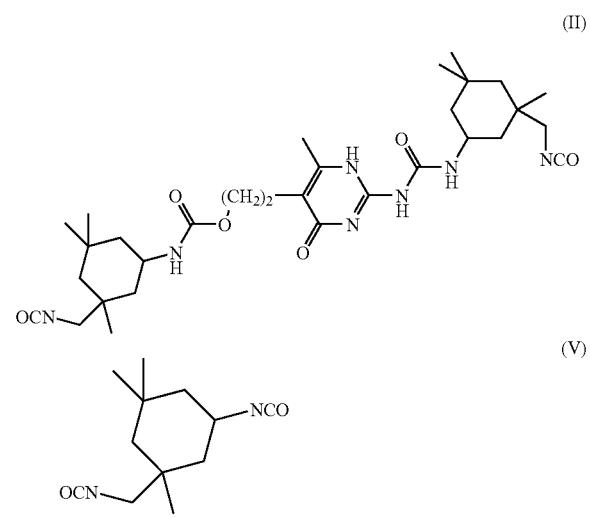

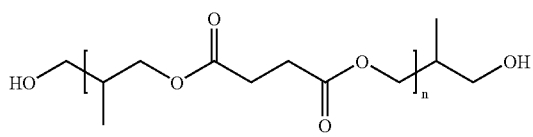

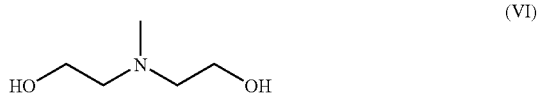

The following were mixed in 250 ml of chloroform:
- 16.3 g (1 equiv) of poly(2-methyl-1,3-propylene-glutarate) of average molecular weight Mn=1.0 kDa (monomer (b1) OH-functionalized telechelic polyester diol of formula (IV)),
- 7.1 g (1 equiv) of isophorone diisocyanate of formula (V),
- 8.4 g (6/7 equiv) of monomer of formula (II) prepared in Example 1, and
- 3.6 g (1 equiv) of N-methyl-diethanolamine of formula (VI) (monomer (b2)).

A few drops of dibutyl tin dilaurate (catalyst) were added. The mixture was heated at 60° C. for 16 hours. The polymer was precipitated in hexane and then dried at reduced pressure.

The desired polymer was obtained at a yield of 96%.

The number-average molecular weight (Mn) of the polymer obtained was about 13 000 Da.

EXAMPLE 3

Nail Varnish Composition 4.8 g of polymer obtained in Example 2 was dissolved in 30 ml of THF, 22 g of butyl acetate was added, then the THF was evaporated.

A viscous solution was obtained, which contained 17.9 wt. % of polymer.

The viscosity was lowered, as required, by adding up to 2 g of ethanol.

After application of this solution on a nail, a shiny, transparent film was obtained.

EXAMPLE 4

Hair Spray Composition 16 g of polymer obtained in Example 2 was dispersed in water according to the following method: 16 g of polymer was dissolved in 64 g of THF, obtaining a viscous medium. 10 g of ethanol and then 14.4 g of 1 N HCl were added to neutralize all of the groups from the N-methyl-diethanolamine. Then 76.3 g of water were added while stirring with a magnetic bar, at room temperature. Then the THF and the ethanol were evaporated at 50° C., in a rotary evaporator.

A clear, slightly yellowish solution of low viscosity was obtained.

Final dry extract: 18.4% (by weight).

Particle size measured by diffusion of light after considerable dilution (using a Coulter N4-SD instrument): 30 nm.

pH=2.3.

The dispersion of polymer in water thus obtained was then put in a pump-spray and sprayed on the hair. The product gave long-lasting fixing of the hair. The hair was shiny.

EXAMPLE 5

Preparation of a Polyurethane-polyurea-poly(ethylene-butylene) Copolymer Bearing an Ionizable Function 26.2 g of hydrogenated di-OH 1,2-polybutadiene (GI3000 from Nisso-PB, Mn=3100) was dissolved in a dried mixture of 120 ml of toluene and 20 ml of pyridine, in the presence of 3.81 g of N-methyldiethylethanolamine, 7.12 g of isophorone diisocyanate (V), and 3 drops of catalyst (dibutyltin dilaurate). The reaction mixture was heated at 80° C. under argon for 2 hours.

Then the monomer (II) prepared in Example 1 was added to this solution. The mixture was heated for a further 16 hours.

The reaction mixture was concentrated to 50% of the initial volume by evaporation under vacuum, 50 ml of toluene was added and evaporated again, repeating the operation twice.

Then the mixture was dissolved in a chloroform/methanol mixture (9 volumes/1 volume). The desired polymer was obtained by precipitation in a large volume of methanol (excess of 10 volumes). The precipitate was filtered and dried it under vacuum.

40.2 g of the required polymer was obtained, and was characterized by GPC (THF): its molecular weight was Mn=9.6 kDa with a dispersity index of 1.7.

The solution was then placed in a pump-spray and sprayed on the hair. Long-lasting fixing of the hair was observed. The hair was shiny.

EXAMPLE 6

Hairdressing Composition 15.4 g of the polymer from Example 5 was dissolved in 46.2 g of THF, then 11.6 g of 1 N HCl and 87.3 g of water were added. The dispersion was evaporated in the rotary evaporator to 50% under vacuum to obtain an aqueous dispersion.

Final dry extract: 13.8% (by weight). Particle size measured by diffusion of light (using a Coulter N4-SD instrument) (after considerable dilution): 300 to 500 nm.

pH=2.7.

EXAMPLE 7

Preparation of a Polyurethane-polyurea-polyester Copolymer Bearing a Carboxylic Acid Ionizable Function

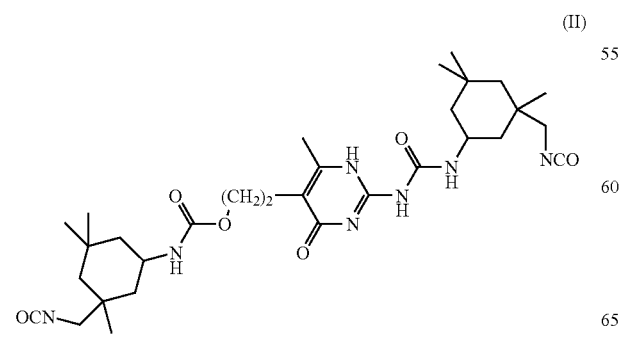

(II)

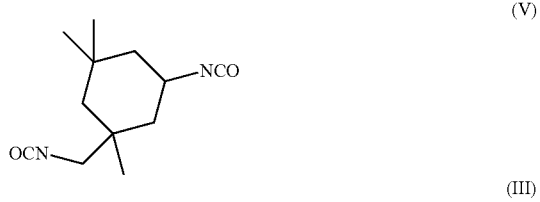

(V)

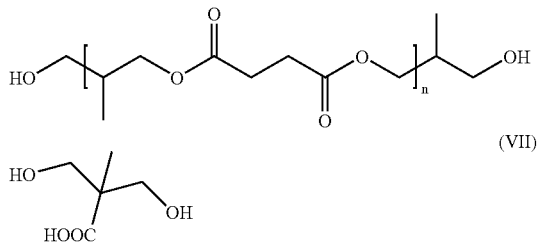

(III)

(VII)

A mixture of 13 g of poly(2-methyl-1,3-propylene-glutarate) (III) of Mn=1 kDa and 3.42 g of 2,2-bis(hydroxymethyl)propionic acid (VII) was dried under vacuum at 110° C. for 2 hours and then dissolved in a previously dried solvent mixture (40 ml of toluene+40 ml of methyl ethyl ketone) in the presence of 5.66 g of isophorone diisocyanate (V) and a catalytic amount of dibutyltin dilaurate (3 drops).

Then the reaction mixture was heated at 80° C. under argon for 2 hours, followed by addition of 6.70 g of monomer (II).

The mixture thus obtained was heated for a further 16 hours, under argon. 10 ml of methanol was added to the reaction mixture, then the desired polymer was precipitated in a large excess of hexane. The polymer was filtered and then dried at reduced pressure, obtaining 28.3 g of the required polymer, characterized by GPC (THF): its molecular weight was Mn=5.3 kDa with a dispersity index of 2.5.

EXAMPLE 8

Nail Varnish Composition 9.3 g of the polymer obtained in Example 7 was dissolved in 40 g of ethyl acetate in the presence of 9 g of ethanol, after heating at 50° C. for 15 hours. This solution gave shiny films after application on the surface of a nail.

EXAMPLE 9

Preparation of a Polyurethane-Polyurea-Polyester Copolymer without Ionizable Functions

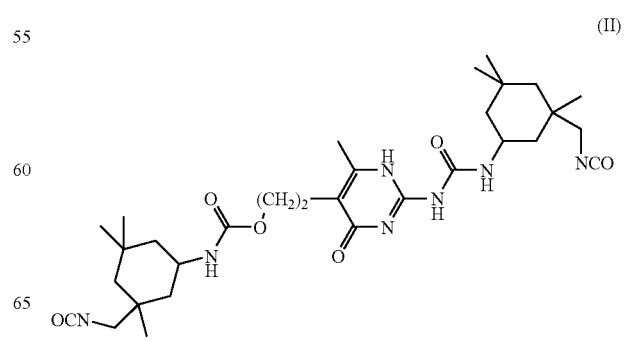

(II)

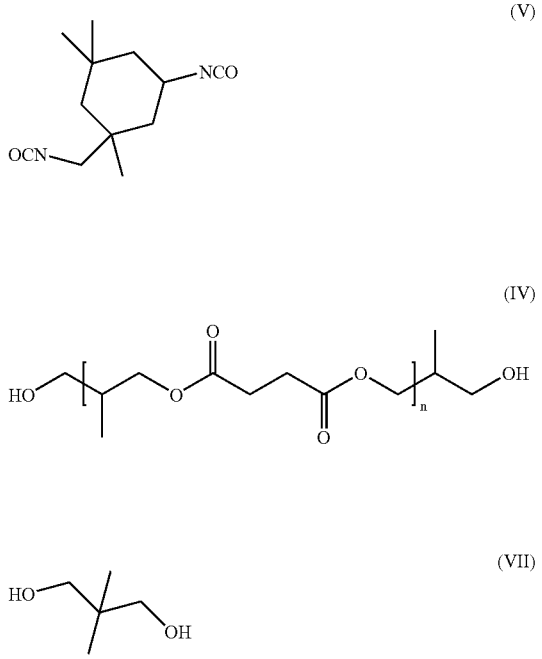

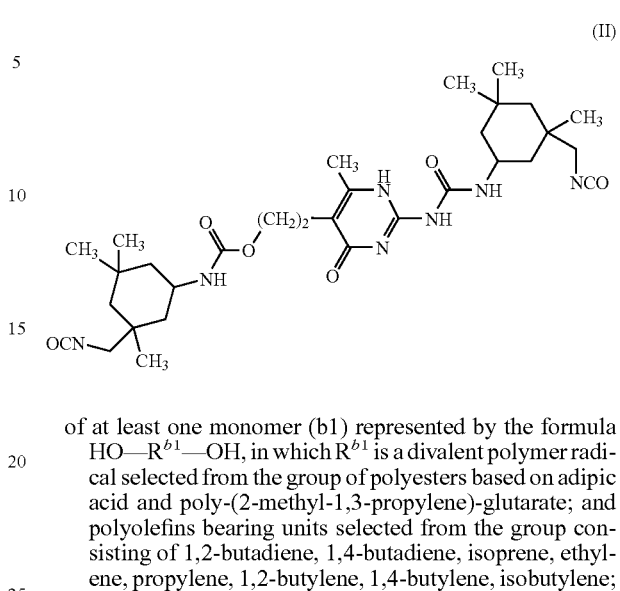

A mixture of 14.8 g of poly(2-methyl-1,3-propylene-glutarate) Mn=1 kDa (IV) and 3.03 g of 2,2-dimethyl-1,3-propanediol (VII) was dried under vacuum at 110° C. for 2 hours before being dissolved it in a mixture of 60 ml of dry toluene+40 ml of methyl ethyl ketone, in the presence of 6.74 g of isophorone diisocyanate (V) and a catalytic amount of dibutyltin dilaurate (3 drops).

Then the reaction mixture was heated at 80° C. under argon for 2 hours, and then 7.65 g of monomer (II) was added.

The mixture thus obtained was heated for a further 16 hours, under argon. 10 ml of ethanol was added to the reaction mixture, then the polymer was precipiated in a large excess of hexane. The polymer was filtered and then dried under vacuum, obtaining 31.4 g of the required polymer, characterized by GPC (THF): its molecular weight was Mn=9.3 kDa with a dispersity index of 2.5.

EXAMPLE 10

Nail Varnish Composition 9.18 g of the polymer from Example 9 was dissolved in 40 g of ethyl acetate in the presence of 9 g of ethanol, after stirring and heating at 50° C. for 15 hours. This solution gave shiny films after application on the surface of a nail.

What is claimed is:

1. A cosmetic composition comprising:
   a physiologically acceptable medium, and
   a copolymer, in said medium, having a (thio)urethane/(thio)urea polymer skeleton, resulting from the reaction:
   of monomer (a) having the structure ((II)

of at least one monomer (b1) represented by the formula HO—$R^{b1}$—OH, in which $R^{b1}$ is a divalent polymer radical selected from the group of polyesters based on adipic acid and poly-(2-methyl-1,3-propylene)-glutarate; and polyolefins bearing units selected from the group consisting of 1,2-butadiene, 1,4-butadiene, isoprene, ethylene, propylene, 1,2-butylene, 1,4-butylene, isobutylene; and 1,2-butadiene, wherein monomer (b1)has a weight-average molecular weight (Mw) ranging from 500 to 30,000; and
   of at least one ionizable monomer (b2) selected from the group consisting of N-methyldiethanolamine; N-tert-butyldiethanolamine; N-ethyldiethanolamine; dimethylolpropionic acid; dimethylaminopropionic acid;, N-ethylsulphonic-dimethanolamine and N-ethylsulphonic-diethanolamine.

2. The cosmetic composition according to claim 1, wherein the at least one monomer (b1) has a weight-average molecular weight (Mw) ranging from 800 to 15,000.

3. The cosmetic composition according to claim 1, wherein:
   the at least one ionizable monomer (b2) is present in an amount ranging from 3 to 20 wt.%, of the total weight of the final copolymer.

4. The cosmetic composition according to claim 1, wherein the at least one ionizable monomer (b2) is present in an amount ranging from 8 to 15 wt.% of the total weight of the final copolymer.

5. The cosmetic composition according to claim 1, wherein the copolymer has a polymer skeleton having a degree of polymerization in the range from 3 to 20,000.

6. The cosmetic composition according to claim 5, wherein the copolymer has a polymer skeleton having a degree of polymerization in the range from 10 to 5,000.

7. The cosmetic composition according to claim 1, wherein the copolymer has a number-average molecular weight Mn ranging from 1,000 to 3,000,000.

8. The cosmetic composition according to claim 7, wherein the copolymer has a number-average molecular weight Mn ranging from 8,000 to 500,000.

9. The cosmetic composition according to claim 1, wherein the molar ratio of monomer (a) to the at least one monomer (b1) and the at least one ionizable monomer (b2) is 1.

10. The cosmetic composition according to claim 1, wherein the at least one monomer (b1) is present in an amount ranging from 10 to 95 wt.% of the total weight of the final polymer.

11. The cosmetic composition according to claim 10, wherein the at least one monomer (b1) is present in an amount ranging from 15 to 80 wt.% of the total weight of the final polymer.

12. The cosmetic composition according to claim 1, wherein the copolymer is present in a form that is soluble or dispersible in the physiologically acceptable medium.

13. The cosmetic composition according to claim 1, wherein the physiologically acceptable medium comprises a medium that is a solvent of the copolymers comprising at least one component chosen from water, alcohols, polyols, esters, carbon-containing oils, silicone oils, fluorinated silicone oils, and mixtures thereof.

14. The cosmetic composition according to claim 1, wherein the physiologically acceptable medium additionally comprises at least one constituent chosen from waxes, gums, surfactants, thickeners, hydrophilic or lipophilic gelling agents, cosmetic actives, preservatives, antioxidants, perfumes, luster agents, fillers, neutralizing agents, emulsifiers, co-emulsifiers, pigments, nacres, water-soluble dyes, fat-soluble dyes, and polymers.

15. The cosmetic composition according to claim 1, wherein the physiologically acceptable medium additionally comprises at least one film forming polymer.

16. The cosmetic composition according to claim 1, wherein the copolymers, alone or mixed, are present in an amount ranging from 0.01 to 90 wt% relative to the total weight of the composition.

17. The cosmetic composition according to claim 16, wherein the copolymers, alone or mixed, are present in an amount ranging from 0.5 to 80 wt% relative to the total weight of the composition.

18. The cosmetic composition according to claim 1, wherein it is in the form of a product for care, cleaning and/or make-up of the skin of the body or of the face, of the lips, eyelashes, nails and hair; a tanning or self-tanning product; a body hygiene product; a hairdressing product for care; cleaning, styling, shaping, or coloring of hair.

19. A method of cosmetic treatment of kerationous matreials, comprising applying to the keratinous materials the cosmetic composition according to claim 1.

20. The method according to claim 19, wherein the cosmetic treatment is for make-up, care, cleaning or coloring of the skin of the body or of the face, the nails, eyelashes and hair.

21. The cosmetic composition according to claim 1, wherein which $R^{b1}$ is a polyester based on adipic acid.

22. The cosmetic composition according to claim 21, wherein monomer (b2) is N-methyldiethanolamine.

23. The cosmetic composition according to claim 1, wherein monomer (b2) is N-methyldiethanolamine.

24. The cosmetic composition according to claim 1, wherein the molar ratio of the monomer (a) to the at least one monomer (b1) and the at least one ionizable monomer (b2) ranges from 0.5 to 2.

25. The cosmetic composition according to claim 1, wherein the at least one ionizable monomer (b2) is present in an amount ranging from 1 to 30 wt.% of the total weight of the final polymer.

* * * * *